(12) United States Patent
Moody et al.

(10) Patent No.: US 10,813,981 B2
(45) Date of Patent: Oct. 27, 2020

(54) SAPOSIN B BINDS THE LIPOFUSCIN BISRETINOID A2E AND PREVENTS ITS ENZYMATIC AND PHOTO DEGRADATION

(71) Applicants: Kelsey Moody, LaFayette, NY (US); Robert P. Doyle, Manlius, NY (US)

(72) Inventors: Kelsey Moody, LaFayette, NY (US); Robert P. Doyle, Manlius, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 15/886,640

(22) Filed: Feb. 1, 2018

(65) Prior Publication Data

US 2018/0221455 A1    Aug. 9, 2018

Related U.S. Application Data

(60) Provisional application No. 62/454,641, filed on Feb. 3, 2017.

(51) Int. Cl.
| | | |
|---|---|---|
| *A61K 38/44* | (2006.01) |
| *A61P 27/02* | (2006.01) |
| *A61K 9/00* | (2006.01) |
| *A61K 31/685* | (2006.01) |
| *A61K 31/122* | (2006.01) |
| *A61K 31/4425* | (2006.01) |
| *A61K 31/11* | (2006.01) |
| *A61K 31/4706* | (2006.01) |

(52) U.S. Cl.
CPC ............ *A61K 38/44* (2013.01); *A61K 9/0051* (2013.01); *A61K 31/11* (2013.01); *A61K 31/122* (2013.01); *A61K 31/4425* (2013.01); *A61K 31/4706* (2013.01); *A61K 31/685* (2013.01); *A61P 27/02* (2018.01); *C12Y 111/01007* (2013.01)

(58) Field of Classification Search
CPC ..................................................... A61K 38/44
See application file for complete search history.

(56) References Cited

PUBLICATIONS

Liu et al., The J of Histochemistry and Cytochemistry, 1995, 43(5):489-495.*
Wu et al. J of the American Chemical Society, 2011, 133:849-857.*

* cited by examiner

*Primary Examiner* — Bin Shen
(74) *Attorney, Agent, or Firm* — David L. Nocilly; Bond Schoeneck & King, PLLC

(57) ABSTRACT

Disclosed herein are methods and compositions useful in the treatment and/or prevention of a disease or indication associated with accumulation of a bisretinoid, for example A2E. In many embodiments, the disclosed methods and compositions are useful in treating an eye disease, for example macular degeneration.

11 Claims, 18 Drawing Sheets
(15 of 18 Drawing Sheet(s) Filed in Color)

PRIOR ART

US 10,813,981 B2

SAPOSIN B BINDS THE LIPOFUSCIN BISRETINOID A2E AND PREVENTS ITS ENZYMATIC AND PHOTO DEGRADATION

CROSS-REFERENCE TO RELATED APPLICATION

This application claims the benefit under 35 U.S.C. § 119 to U.S. Provisional Application No. 62/454,641 entitled "SAPOSIN B BINDS THE LIPOFUSCIN BISRETINOID A2E AND PREVENTS ITS ENZYMATIC AND PHOTO DEGRADATION," filed Feb. 3, 2017; the entirety of which is hereby incorporated by reference for all purposes.

FIELD

The disclosed processes, methods, and compositions are directed to enhancing degradation of bisretinoid accumulation. In many embodiments, the disclosed methods and compositions may be useful in treating one or more diseases associated with intracellular and extracellular accumulation of A2E.

BACKGROUND

The eye is a complex organ comprising a variety of specialized structures, tissues, and cells. Light enters the eye at the lens and is focused on the back inner wall of the eyeball, the retina. Within the center of the eyeball is a viscous liquid referred to as the aqueous humor, through which light travels to reach the retina. Mammalian eyes, including the human eye, include a structure, the macula, located near the center of the retina, opposite the lens. This is the region of the retina with the highest density of light-detecting cells.

The macula is divided into several regions or areas: the umbo, foveola, foveal avascular zone, fovea, parafovea, and perifovea areas. The fovea, which is located at or near the center of the macula, comprises the eye's largest concentration of cone cells, which are able to distinguish color (rod cells, the other light-sensing cell, do not differentiate light based on color). The fovea, therefore, is responsible for high resolution color vision.

Macular degeneration (MD) is the loss of vision in the center of the visual field. It is typically seen in older people and is the major cause of vision loss and blindness in this population. There are three types of MD: early, intermediate, and late. Late type MD has two forms 'dry' and 'wet'. The dry form accounts for the majority of macular degeneration cases, and is typically the less serious form, caused by the loss of light-sensing cells (photoreceptors) in the macula. This form results from the buildup of cellular debris in the macula. Specifically, the debris accumulates in an area between the retina and an underlying vascular layer, the choroid. This buildup can result in atrophy of cells in the region, as well as scarring of the retina.

The wet form of MD is the more severe form and it usually progresses from the dry form. The wet form is caused by abnormal growth of blood vessels from the choroid (neovascularization). These blood vessels are prone to leakage and/or rupture, leading to blood, protein, and other debris being deposited below the macula. The cellular atrophy, debris buildup, and eventual scarring lead to rapid loss of vision and/or blindness if untreated.

Retinal pigmented epithelial (RPE) cells are essential support cells found in the macula. The RPE cells are important in that they support the light sensitive photoreceptor cells. In MD, RPE cells experience an accumulation of debris, termed lipofuscin, within the cell. This accumulation of lipofuscin affects the ability of RPE cells to properly support the photoreceptor cells. Failure of RPE cells leads to death of the photoreceptors and a progressive loss of vision. Extracellular accumulations of debris, termed drusen, increase in size and quantity as MD progresses. Lipofuscin mediated RPE cell death is thought to contribute to drusen formation. As drusen accumulates, it can destabilize the macular region by contributing to inflammation, complement activation, and other processes. Thus, over time, dry MD progresses to the wet form of macular degeneration, also referred to as neovascular macular degeneration.

In some diseases, including MD, lipofuscin may accumulate to significant levels in RPE cells. This accumulation is typically the result of dis-regulation of vitamin A recycling. Major lipofuscin constituents include the bisretinoid N-retinylidene-N-retinylethanolamine (A2E; FIG. 1 top) and its photoisomers, which have adverse effects due to their amphiphillicity and photoreactivity. In addition to MD, A2E accumulation in the lysosomes of cells of the retinal pigment epithelium (RPE) is seen in patients with Stargardt disease (SD), and Best vitelliform macular dystrophy. A2E has been extensively investigated and is the focus of therapeutic approaches that strive to reverse its accumulation in RPE. In 2011, a seminal proof-of-concept study by Sparrow et al. demonstrated the feasibility of using an 'enzyme-replacement' approach to A2E degradation by introducing horseradish peroxidase (HRP) into a human RPE cell line (ARPE-19), reducing A2E levels by 75%.

A2E research has focused on its role in oxidative stress, but a few studies have demonstrated that A2E can directly interact with endogenous proteins. Work by Moiseyev et al. has demonstrated that A2E can inhibit non-palmitoylated, soluble, cytoplasmic retinoid isomerohydrolase (RPE65 isomerohydrolase) by direct binding ($K_D$ 250 nM). Yanagi et al. have demonstrated A2E to be an endogenous ligand for retinoic acid receptor (RAR), inducing sustained activation of RAR target genes.

What is needed are therapeutic methods and compositions that target A2E accumulation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

SapB is an intra-lysosomal, non-enzymatic proteinaceous co-factor that binds and presents 3-O-sulfogalactosylceramide (sulfatide) to the active site of arylsulfatase A (ASA) for desulfation to galactosylceramide. The lack of functional SapB (or ASA) results in a build-up of sulfatide and the fatal lysosomal storage disease (LSD) metachromatic leukodystrophy (MLD). Surprisingly, Applicants note that progressive RPE degeneration has been reported in some patients with MLD. In addition, Barres et al. has recently shown that sulfatide (but not galactosylceramide) can inhibit optic nerve growth, including the re-growth of damaged optic nerve. SapB has also been shown to 'flush' bound ligand, such as Coenzyme Q10 (CoQ10), in human urine.

SapB was the first of four saposins to be discovered and is a product of the post-translational cleavage of prosaposin, along with SapA, SapC, and SapD. Of the four saposins, only SapB is nonenzymatic. SapB favors a dimeric structure, has a variable degree of α-helical character across pH ranges (~53% at ~lysosomal pH 5; ~68% at pH 7.0), three disulfide bonds, and a hydrophobic binding pocket, consistent with its role in lipid binding.

Previous work has focused on SapB interaction with lipids, lipidlike molecules, and ASA. Applicants have shown that SapB can bind ligands beyond sulfatide. It has been shown that SapB binds coenzyme Q$_{10}$ (CoQ$_{10}$) and serves as a binding and transfer protein for the coenzyme, with [SapB-CoQ10]$_{complex}$ being detected in human urine. It has also been shown that SapB binds the lysosomotropic antimalarial drugs atovaquone (ATO) and chloroquine (CQ), as well as the bisretinoid N-retinylidene-N-retinylethanolamine (A2E), which accumulates in the lysosome of patients with macular degeneration.

The critical importance of SapB as a lysosomal activator and transporter protein and its multiligand binding characteristics beyond sulfatide degradation raise important questions about the driving forces and factors that influence such a wide range of ligand interactions.

Disclosed herein are methods, systems, and compositions for aiding the treatment, amelioration, and/or prevention of diseases and indications related to A2E accumulation. In many embodiments, the A2E-related indications may include eye diseases such as macular degeneration. In some embodiments, the disclosed methods, systems, and compositions may target one or more A2E binding sites allowing proteolytic degradation of A2E. In some embodiments, the disclosed methods, systems, and compositions may include co-administration of an A2E enzyme and an A2E binding molecule. In some embodiments, the A2E binding molecule may bind A2E at or near a SapB binding site. In some embodiments, the A2E binding molecule may be SapB, a fragment of SapB, and/or mutants of SapB.

Figure 11:
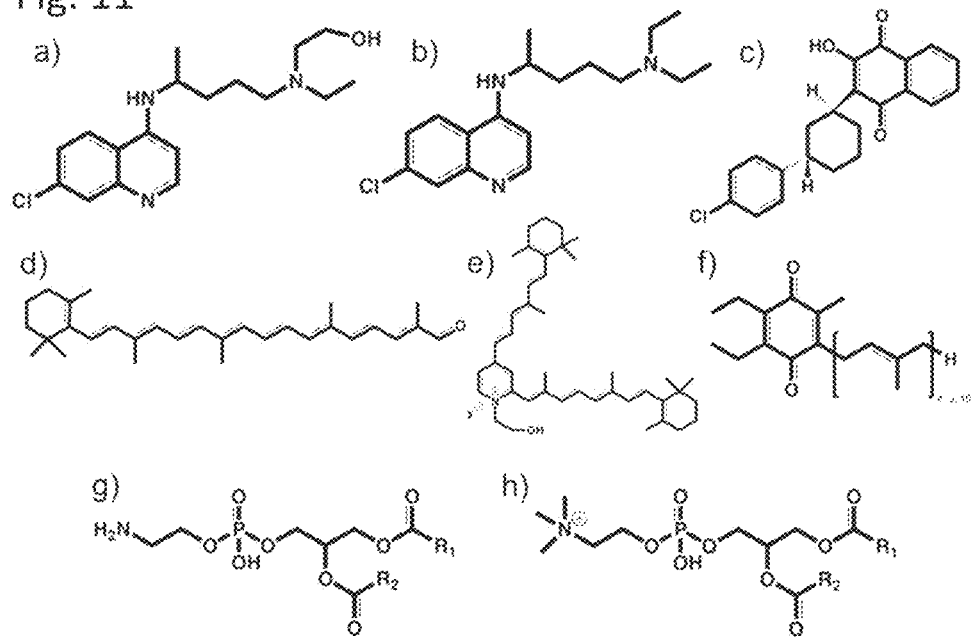
FIG. 11. Shows Scheme 1: Structures of SapB Binding Ligands. Panel a) hydroxychloroquine (HCQ), Panel b) CQ, Panel c) ATO, Panel d) apo-carotenal (ACar), Panel e) A2E, Panel f) Coenzyme Q4, Q9 (CoQ4, CoQ9) or CoQ10, Panel g) phosphatidylethanolamine (PEth) Panel g) phosphatidylcholine (PCho).
Figure 12:
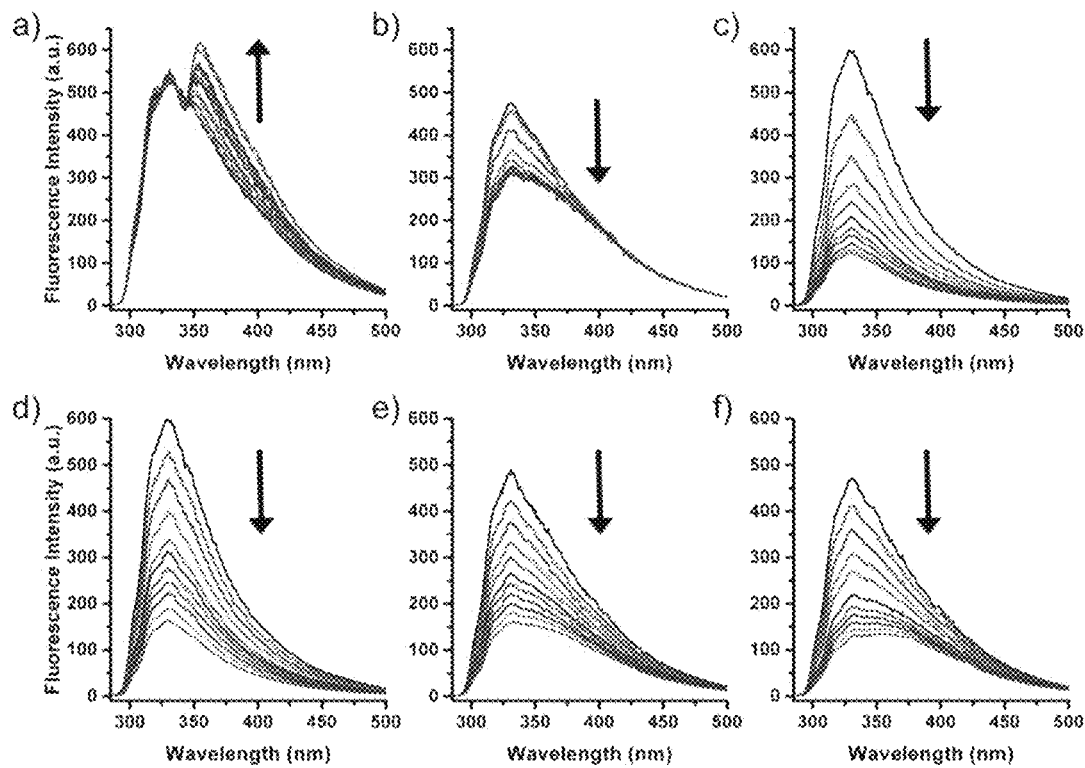
FIG. 12. Spectrophotometric titrations of SapB with varying ligands. Panel a) HCQ, Panel b) ACar, Panel c) PEth, Panel d) PCho, Panel e) CoQ4, Panel f) CoQ9 Conditions: 40 µM SapB in 50 mM phosphate buffer, pH 5.5 with 2 µL injections of 2 mM ligand (50 mM phosphate buffer, pH 5.5 for HCQ; all others in DMF-see experimental section), conducted at room temperature.

Also disclosed, is evidence using fluorescence spectroscopy and computational docking studies, supported by our work using isothermal calorimetry (ITC) and protein crystallography, showing that SapB binds a wide variety of ligands with $K_D$ values ranging from micromolar to nanomolar (see FIGS. 11 and 12). Furthermore, demonstrated herein is the use of a ligand's calculated partition coefficient (Log P) to predict binding affinity with SapB and studies showing that SapB-ligand binding is driven principally by entropic factors.

In some cases, deviation from this general binding model, as in the case of the [SapB-ATO]complex, may be due to the presence of a second, strong binding site for ATO. This second site may also be used for binding other ligands as well. The second binding site has been mapped to the surface of the SapB. This surface binding is shown to block access of other ligands to the deeper binding pocket inside SapB.

Applicants also noted, surprisingly, that A2E-associated, sustained gene activation may in some cases result in neovascularization about the RPE. In addition, a study by Sparrow et al. showed that conditions that promote A2E aggregation (i.e. non-polar environments/microdomains) within the lysosome also promote photooxidation/photodegradation of A2E. Although Sparrow postulated that interactions between A2E and components of the lysosomal milieu might serve to hold a fraction of A2E available for redistribution amongst lysosomal microdomains after photobleaching, they offered no specific examples except to suggest involvement of polar and hydrophobic side-chains of proteins.

Applicants have identified binding sites on A2E that may be targeted to aid in promoting enzymatic destruction of A2E. For example, Applicants disclose that SapB binds A2E ($K_D$=25 μM) with an observed binding stoichiometry of 2:1 SapB:A2E. The binding of SapB to A2E is shown to protect A2E from both enzymatic degradation and photo bleaching.

The disclosed methods, systems, and compositions, in conjunction with a recently described structure of SapB with the lysosomotropic drug chloroquine (CQ), indicate a broader ligand binding scope than previously considered for SapB.

Figure 1:
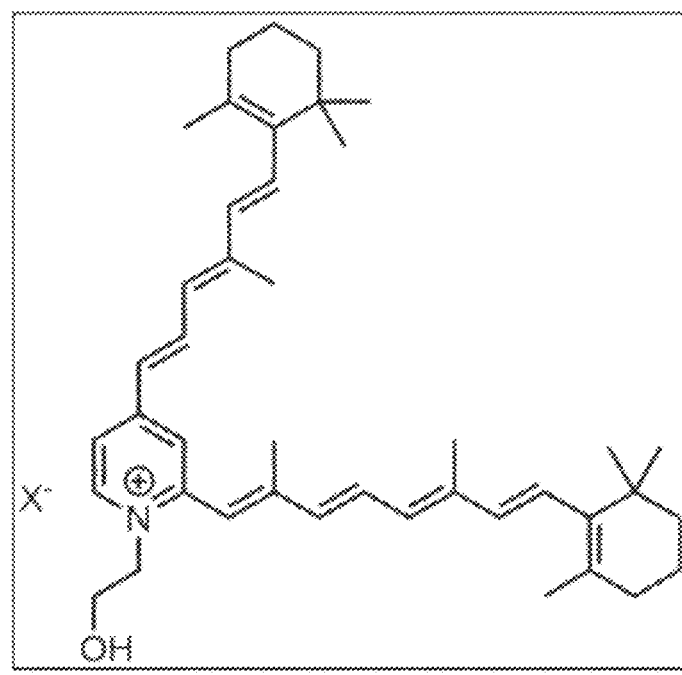
FIG. 1. Structure of the bisretinoid N-retinylidene-N-retinylethanolamine, A2E.
Figure 1:
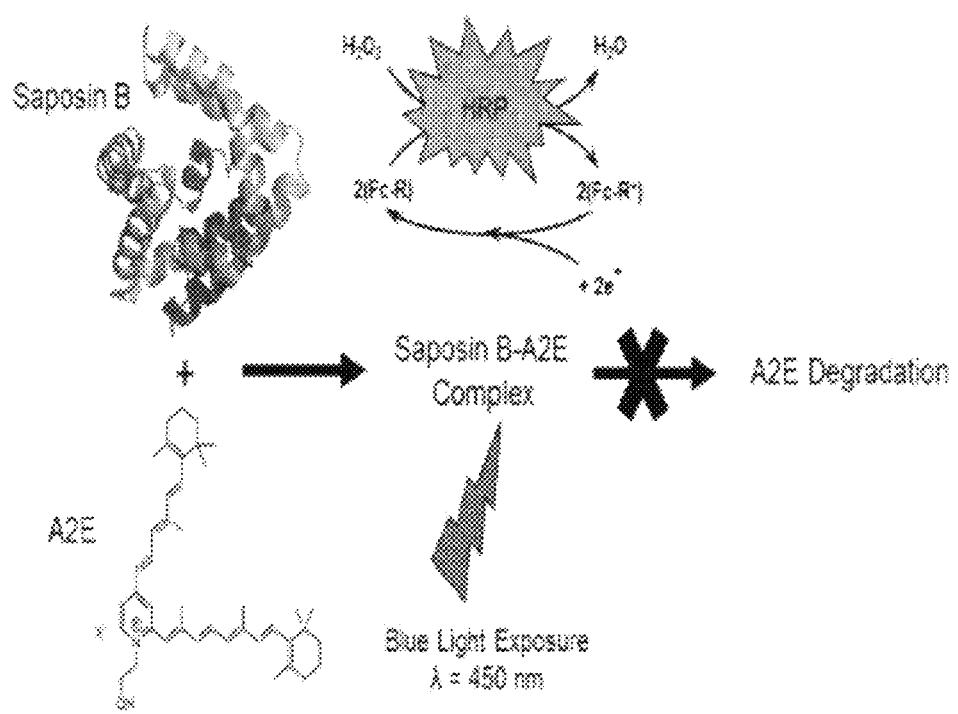

Applicants herein describe targeting of lysosomal accumulation of bisretinoid in the prevention and treatment of macular degeneration. Whether endogenous lysosomal proteins can bind A2E, the primary bisretinoid in lipofuscin granules in retinal pigmented epithelial cells, and interfere with enzymatic or photo induced degradation of A2E has not been previously explored. Herein, Applicants demonstrate that Saposin B, a protein involved in the degradation of sulfatides and 'flushing' of lipids, can bind A2E. This binding is shown to reduce or prevent $H_2O_2$-dependent degradation of A2E by HRP, as well as photo-oxidation/degradation by blue-light (FIG. 1, bottom).

Sap B Binding

The SapB protein can bind A2E and $CoQ_{10}$. The binding sites may be referred to as the A2E binding site, and the CoQ binding site. The region of SapB bound to A2E may be referred to as the SapB:A2E interface. In many embodiments, SapB binding to A2E may prevent or interfere with degradation of A2E. In many embodiments, targeting the SapB binding site with one or more interfering compounds (which may include various molecules, peptides, nucleic acids, peptide-nucleic acid molecules, etc.) may help promote degradation of A2E. In many embodiments, the interfering compound, molecule, or peptide may comprise a structure that may mimic SapB at or near the SapB:A2E interface. In some embodiments, the interfering compound, may bind to all or a part of the SapB:A2E interface. In some embodiments, the interfering compound may also interact with all or part of the $CoQ_{10}$ binding site. In some embodiments the interfering compound is a peptide or peptide mimetic designed to mimic the size, shape, charge, and/or binding characteristics of the all or a portion of a SapB:A2E interface. In some embodiments, the interfering compound may have affinity for A2E and/or SapB.

A2E Degradation

Various degrading compounds and methods (in some cases enzymes) may be useful in reducing the concentration and/or accumulation of A2E. In some embodiments, the A2E is degraded within a cell (intracellular) or outside a cell (extracellular). In some embodiments, the A2E may be degraded in a lysozyme within the cell, and the degrading compound may include one or more lysosomal targeting signals. In some embodiments, the enzyme may be HRP. One or more co-factors may be administered with the degrading compound or method. In one embodiment, the co-factor is selected from DMSA and hydrogen peroxide.

Diseases and Indications

The disclosed methods and compounds may be used to treat or prevent one or more diseases or indications. In many embodiments, the disease or indication is an eye disease. In some embodiments, the eye disease may be associated with accumulation of A2E. In some embodiments, the eye disease may be a mammalian eye disease associated with accumulation of A2E in or around retinal pigment epithelium (RPE) for example macular degeneration, Stargardt disease (SD), and Best vitelliform macular dystrophy. In most embodiments, the patient is a mammal. In one embodiment, the patient is a human.

Methods of Treatment

Disclosed herein are various methods useful in treating or preventing accumulation of a bisretinoid, for example A2E. In some embodiments, an interfering compound may be introduced to an organ or tissue having, or susceptible to accumulations of A2E. In some embodiments, the organ is a human eye. In some embodiments, the tissue may be a macula. The interfering compound may be introduced by various systemic or localized methods, such as intraocular injection. In some embodiments, the degrading compound may be co-administered with the interfering compound. In some embodiments, co-administration may include one or two administrations, for example administration of the interfering compound followed by administration of the degrading compound a short period later. In some embodiments, the degrading compound may be administered before the interfering compound.

EXAMPLES

Example 1 A2E Binding of SapB

Spectrophotometric Titration of SapB with A2E

Figure 2:
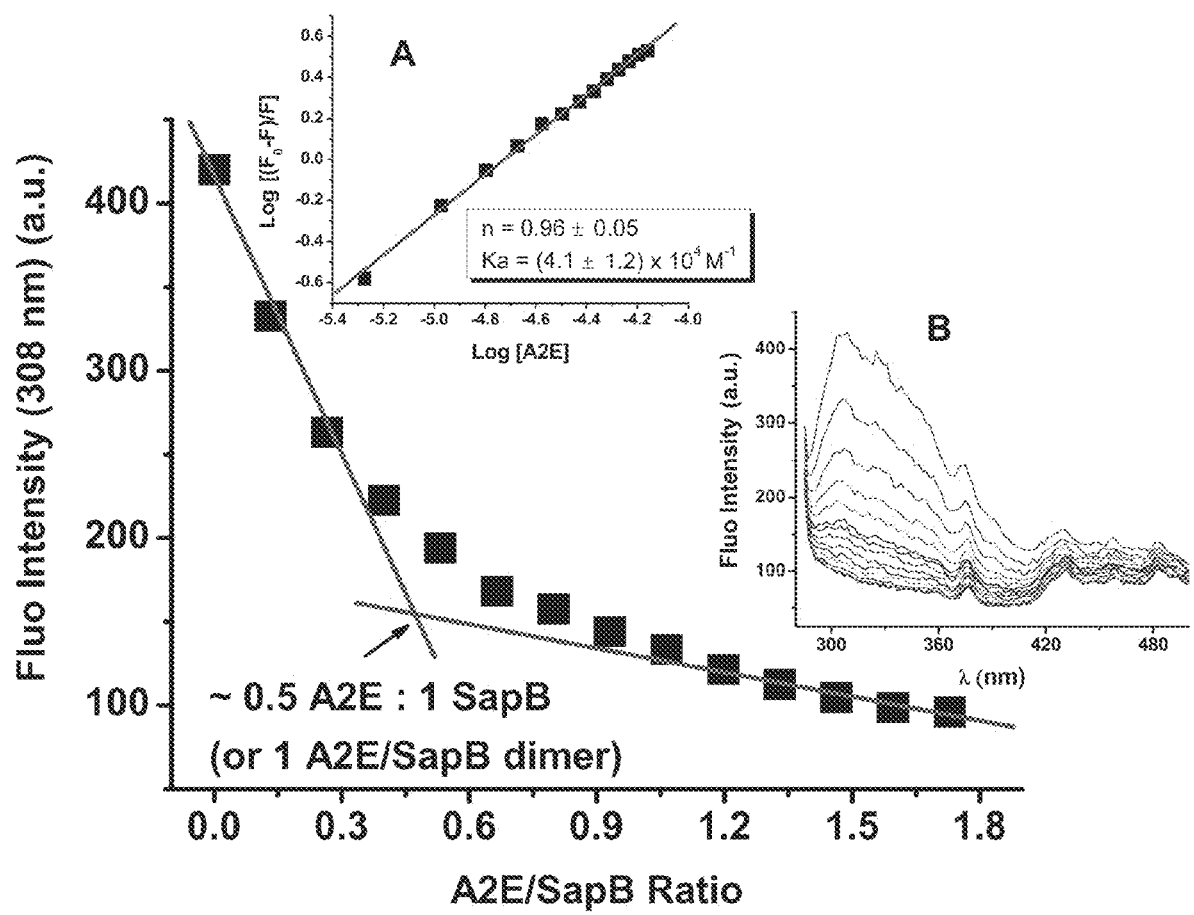
FIG. 2. Spectrophotometric titration of SapB with A2E. Inset A shows a double logarithmic plot of A2E quenching effect on the fluorescence of SapB and inset B shows the titration curves. Conditions: 40 µM SapB, 2 µL injections of 2 mM A2E (0.13 A2E/SapB per injection), 50 mM phosphate buffer, pH 5.5 and 25° C.

A2E and SapB were prepared and purified according to literature reports. To determine the A2E/protein binding stoichiometry, a fluorescence titration was carried out by incrementally adding small amounts of A2E to a solution of SapB (FIG. 2). The quenching of the fluorescence intensity at 308 nm exhibited a discontinuity at ~0.5 A2E/protein, suggesting the formation of a protein-A2E complex with one A2E ligand bound per SapB dimer. A double logarithmic plot of $$\log \frac{(F_0 - F)}{F}$$

versus $\log_{[Q]}$ confirmed a stoichiometry of ~1 A2E per SapB dimer (FIG. 2, inset) and provided a binding affinity ($K_A$) of ~$4 \times 10^6$ M$^{-1}$.

Fluorescence Competition Experiments.

Figure 3:
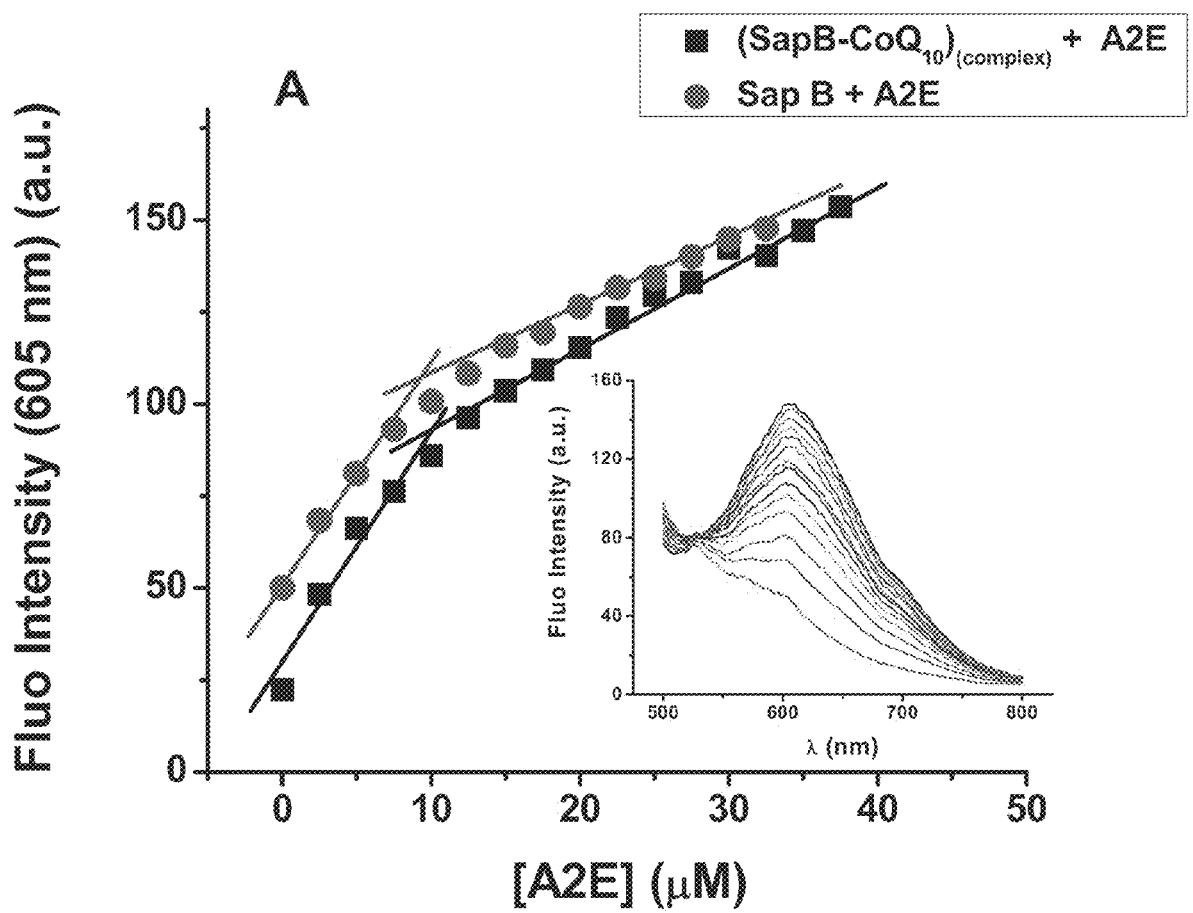
FIG. 3. Spectrophotometric titrations of SapB with A2E in the presence of CoQ10. The insets show the titration curves. Conditions: 20 µM SapB, 1 µL injections of 1.9 mM A2E (0.13 A2E/SapB per injection), 50 mM phosphate buffer, pH 5.5 and 25° C. The (SapB-CoQ10) complex were initially prepared at 2:1 protein:ligand ratio.

We have reported in an earlier study the binding properties of SapB to CoQ10 (a bone fide substrate). To determine whether it binds to the same binding site on the protein or displaces A2E from SapB, a series of fluorescence titration experiments in the presence and absence of $CoQ_{10}$ were performed. FIG. 3 shows an identical fluorescence titration pattern when A2E is titrated into a SapB protein solution alone or a solution of SapB pre-complexed with $CoQ_{10}$, suggesting the, hitherto unknown, presence of a second binding site on SapB, in this case for A2E.

SapB Protects A2E from Damage by HRP.

Horseradish peroxidase (HRP) is reported to cleave the bis-retinoid A2E. Thus, the ability of SapB to protect A2E from oxidative transformations by HRP was investigated. When $H_2O_2$ is added to a solution of A2E containing HRP, a decrease in the absorbance value of A2E at 340 nm is observed (FIG. 4) supporting that A2E acts as a reducing substrate for the HRP/$H_2O_2$ system, as expected.

Figure 4:
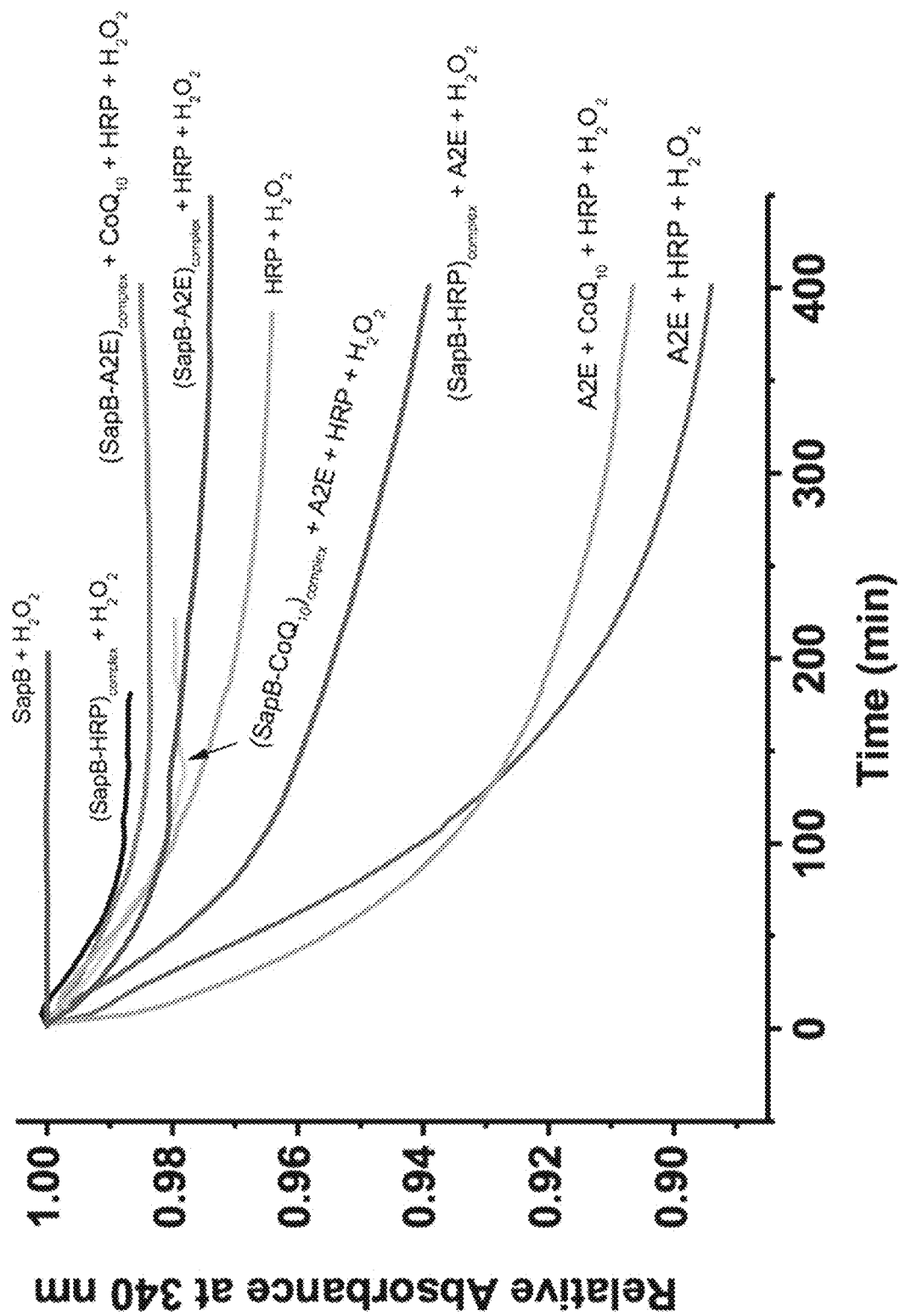
FIG. 4. Kinetic curves following the sequential additions of A2E, HRP, CoQ10, and $H_2O_2$ to SapB as indicated on each curve. Conditions: 12 µM SapB, 6 µM A2E, CoQ10, or HRP, 1 µL of 3% H$_2$O$_2$, 10 µL tween (1% v/v), 50 mM phosphate buffer, pH 5.5 and 25° C.

These experiments were repeated in the presence of A2E pre-complexed with SapB (2:1 SapB:A2E ratio), the absorbance change was very similar to that of a control mixture of HRP and $H_2O_2$ (FIG. 4) indicating a protective role of SapB for A2E. Interestingly, addition of $H_2O_2$ to a SapB-HRP solution (at 1:1 SapB:HRP ratio) resulted in minimal absorbance change indicating a possible protein-protein interaction (see FIG. 7, below) that also protects HRP from $H_2O_2$ induced oxidative damage (FIG. 4). In classic peroxidases, it is believed that reaction with hydrogen peroxide gives rise to two oxidizing equivalents (i.e. a porphyrin radical-cation and an Fe(IV)-oxo (ferryl) species) due to exposure of the prosthetic heme group to the bulk solution. On the other hand, the addition sequence (SapB+HRP)$_{complex}$+A2E+$H_2O_2$ showed partial damage to A2E (FIG. 4) presumably because the porphyrin radical-cation undergoes an electron transfer reaction with the surrounding protein to form a SapB protein radical species. Having established the presence of two different binding sites on SapB (one for A2E and one for $CoQ_{10}$), the ability of SapB to protect A2E in the presence of $CoQ_{10}$ was tested. The addition sequence (SapB+A2E)$_{complex}$+$CoQ_{10}$+HRP+$H_2O_2$ or the sequence (SapB+$CoQ_{10}$)$_{complex}$+A2E+HRP+$H_2O_2$ showed absorbance values similar to the sequence (SapB+A2E)$_{complex}$+HRP+$H_2O_2$, a result in strong support of the fluorescence data of FIG. 3. By comparison, a control experiment consisting of the addition sequence A2E+$CoQ_{10}$+HRP+$H_2O_2$ exhibited a similar absorbance curve to that in the absence of $CoQ_{10}$ (FIG. 4), indicating A2E degradation.

Effect of A2E and SapB on the Formation of Verdoheme (P-670) from Compound III.

Figure 5:
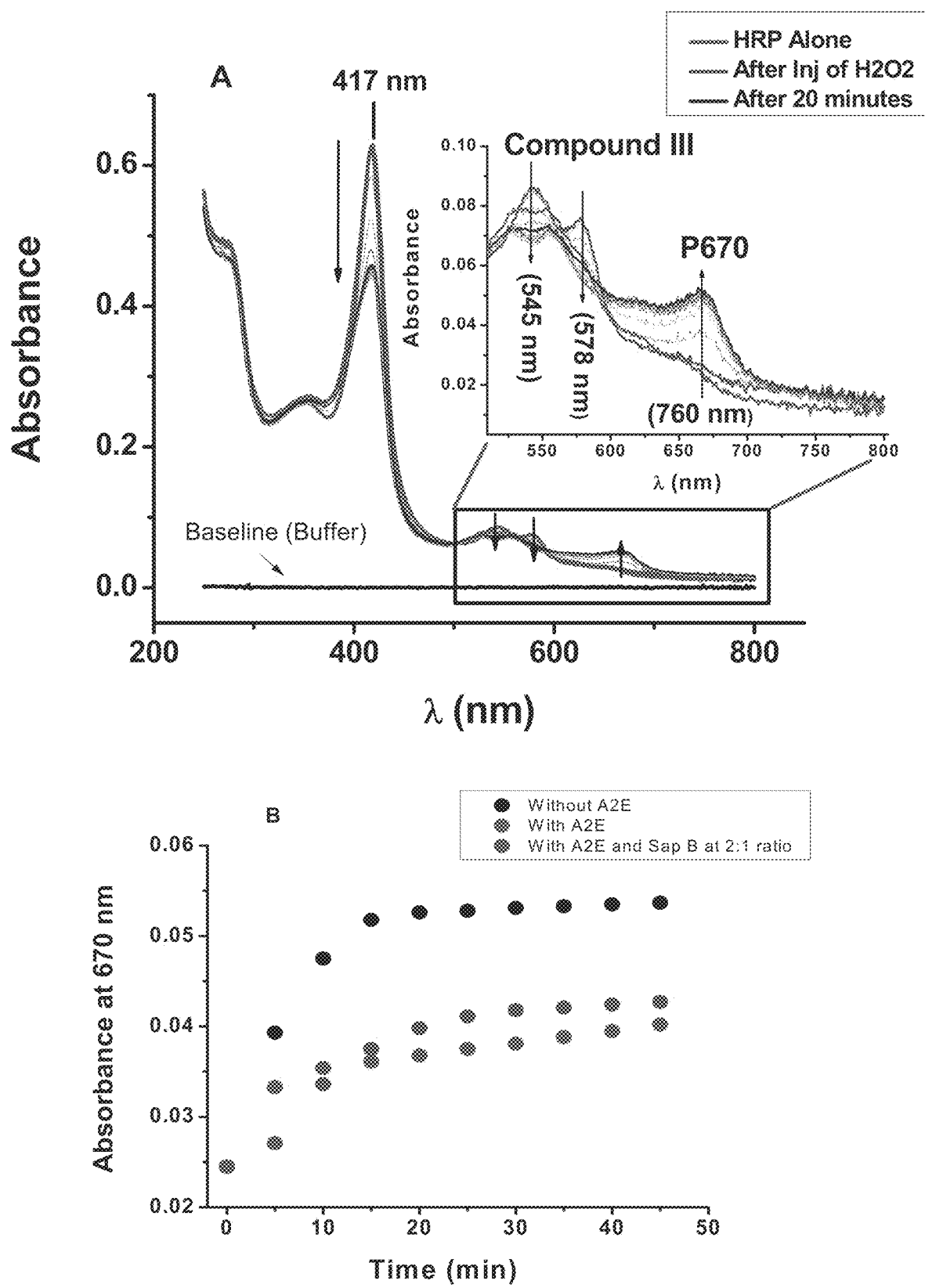
FIG. 5. (A) UV-vis spectral features of HRP (10 µM) following the addition of H$_2$O$_2$ (100 µM) and (B) Absorbance change as a function of time of P670 in the absence and presence of 12 µM A2E and SapB-A2E complex (24 µM SapB: 12 µM A2E). Conditions: 20 mM phosphate buffer, 1% tween, pH 5.5, 25° C.

The peroxidase catalytic cycle of HRP in the presence of $H_2O_2$ and suitable substrates is known to readily convert the native enzyme to the inactive Compound III followed by the generation of verdohemoprotein (or P-670 pigment). Here, and in light of the kinetic results of FIG. 4, we followed the absorbance change at 670 nm to test the hypothesis of whether A2E may be a suitable substrate for the HRP/$H_2O_2$ system. In the presence of excess $H_2O_2$ (100 µM/10 molar equivalents), the UV-vis spectra of HRP showed absorbance maxima at 417, 545, and 578 nm (FIG. 5) indicating the formation of Compound III. The Soret band at 417 nm quickly decreased in intensity with a concomitant increase of a new band at 670 nm, characteristic of verdoheme (P-670) formation. Successive scans (5 min apart) showed that Compound III was not very stable at pH 5.5.

The simultaneous change in absorbance (decrease of the 545 and 578 nm bands and increase of the 670 nm band) implies a full conversion of Compounds III to P-670 both of which maximize at ~20 minutes.

The experiments were then repeated in the presence of A2E and SapB to examine their effect on P-670 formation. The data of FIG. 5B show a significant reduction in the amount of verdoheme formation consistent with a normal peroxidase mechanism with A2E as the reducing substrate. That the data in the presence of A2E alone is similar to that when pre-complexed with SapB suggest that A2E is somewhat exposed to the bulk solution unlike, for example, CQ, which was observed to be buried inside the 'V-shaped' SapB dimer.

Effects of SapB Binding to A2E on Blue-Light Photo-Degradation.

Figure 6:
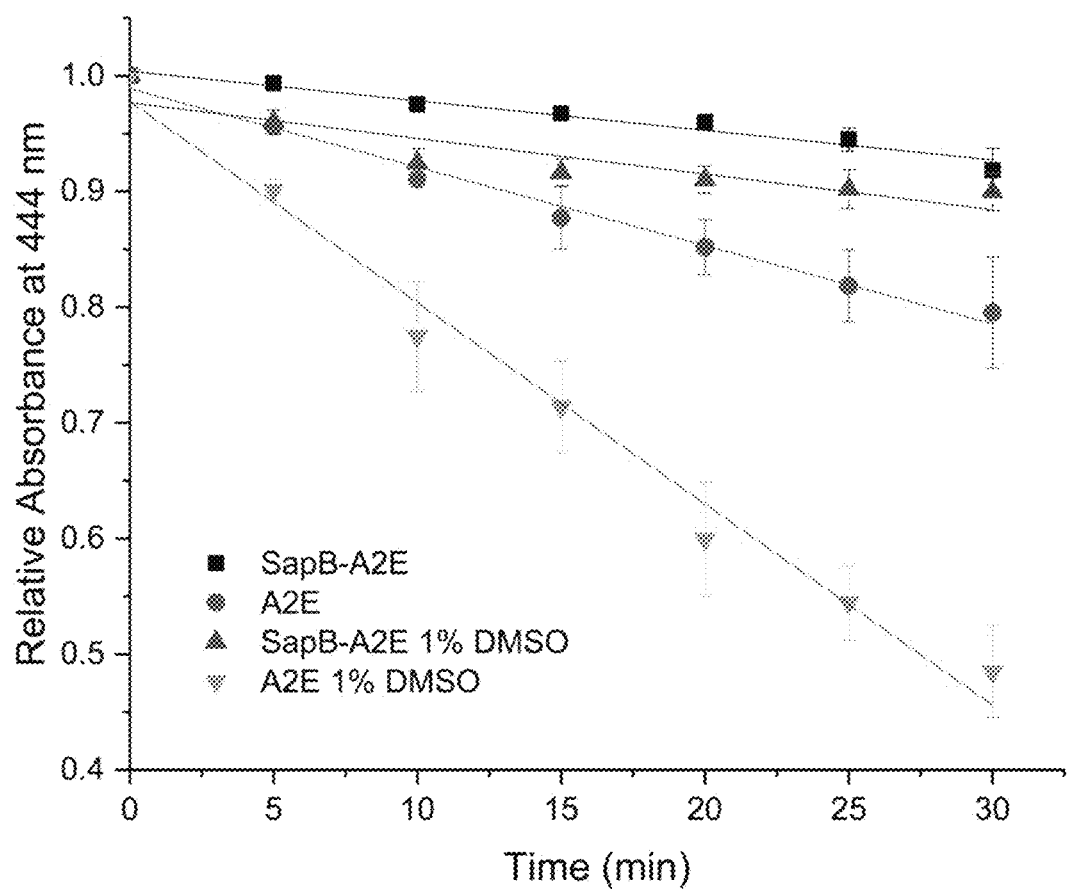
FIG. 6. Effect of 450±10 nm blue light on A2E, free or bound to SapB followed over 30 minutes at 444 nm in 50 mM phosphate buffer with/without 1% DMSO (pH 5.5).

We screened A2E photostability to blue light, whether in its free form or complexed to SapB (2 sapB:1 A2E) (see supplementary materials for details) with and without 1% DMSO (a known facilitator of blue induced photobleaching). The negative decline in slopes (FIG. 6), indicative of A2E degradation over time, was significantly reduced when bound to SapB, supporting the Sparrow hypothesis discussed earlier. The fact that SapB might play a role in mitigating photo-bleaching and providing a source of subsequent fluorescence is an interesting possibility, particularly in light of recent studies by Yamamoto et al. showing that SapB could regulate CoQ10 movement/levels within HepG2 cells.

These experimental results demonstrated that A2E binding by the lysosomal protein SapB prevents A2E degradation by HRP and by blue light. Such binding may complicate attempts to produce an enzyme replacement therapy for A2E degradation and/or play a role in the 'transport' or movement of A2E inside the cell (and possibly out of the cell).

In some cases, an assay may be performed to test the urine of patients with MD or SD for the presence of sapB:A2E complexes. In some embodiments, SapB:CoQ10 has been found in urine.

A2E does not interfere with ASA specific activity albeit at a set time-point (without time-dependent inhibition assays, accounting for equilibrium rates of the binding partners involved or knowledge of A2E interaction with the activator (i.e. SapB)). Subsequent studies demonstrated that it is likely a delay in activity of such hydrolases that results in gradual, long-term accumulation of lipids. Louis et al. demonstrated that activator dependent hydrolysis of myelin cerebroside sulfate by ASA could be affected in terms of slower hydrolysis rates by competition for activator by unidentified "other lipoidal constituents." Applicants hypothesized that SapB binding of A2E may result in competition between A2E and ASA for activator, even temporarily. In some embodiments, sulfatide build-up may be monitored in certain patients, for example patients with MD or SD.

Recombinant Expression of SapB

Recombinant SapB was expressed in E. coli as previously described.

Synthesis and Purification of A2E

A2E was synthesized using a previously described method and purified via standard protocol.

Fluorescence Binding of SapB to $CoQ_{10}$ with no A2E Blocking

Experimental Details

An 800 µL, 20 µM SapB to 10 µM $CoQ_{10}$ complex was made in pH 5.5 50 mM phosphate buffer. The complex was formed at room temperature in a 1 mL glass vial with gentle stirring for 10 minutes. The entire solution was then transferred to a clear fluorescence cuvette. Fluorescence experiments were performed under emission conditions on a Cary Eclipse Fluorescence Spectrophotometer, with an excitation wavelength of 444 nm, emission wavelength range of 500-800 nm, excitation slit width set to 10 nm, and emission slit width set to 10 nm. A baseline scan of SapB-CoQ10 was performed and was then followed by 15, 1 µL injections of 1.90 mM A2E in DMSO, for final total of 16 scans. Analysis of A2E binding the SapB-CoQ10 complex was performed by tracking fluorescence intensity at A2E's peak emission wavelength of 602 nm and plotting it against the concentration of A2E added per each injection.

Fluorescence Binding of SapB to Retinyl Palmitate (RP) and Blocking of A2E Binding Experimental Details Lyophilized SapB was re-suspended in pH 5.5 50 mM phosphate buffer to create a SapB stock. The concentration of the stock solution was determined to be 0.28435 mM via uv-vis absorbance at 278 nm with an extinction coefficient of 2920 $M^{-1}cm^{-1}$. For the fluorescence binding study, the stock was diluted in pH 5.5 50 mM phosphate buffer to reach a final concentration of 40 µM SapB in 1 mL of pH 5.5 50 mM phosphate buffer.

A primary retinyl palmitate stock was prepared by suspending 0.055 g of retinyl palmitate in 1 mL DMF. This stock solution was determined to have a concentration of 104.79 mM by mass.

A purified A2E stock in 1 mL DMSO was determined to have a concentration of 1.1 mM via uv-vis at 436 nm with an extinction coefficient of 36900 $M^{-1}cm^{-1}$. This stock solution was then used to make another stock with a final concentration of 92.8 µM in 1 mL DMSO, confirmed again via uv-vis.

TABLE 1

Summary of Analyte Concentrations and Conditions for SapB-RP + A2E Block

| Analyte | Primary Stock Conc. | Experimental Stock Conc. |
|---|---|---|
| Saposin B | 0.28435 mM | 0.040 mM |
| Retinyl Palmitate | 104.79 mM | 104.79 mM |
| A2E | 1.1 mM | 0.0928 mM |

A SapB-RP complex was formed by adding 4 µL of the experimental stock to 1 mL of the SapB experimental stock for a final volume of 1004 µL in a 1.5 mL Eppendorf tube. The solution was gently rotated at room temperature, in foil, for 15 minutes. The entire 1004 µL was then transferred to a clear fluorescence cuvette. Fluorescence experiments were performed under emission conditions on a Cary Eclipse Fluorescence Spectrophotometer, with an excitation wavelength of 444 nm, emission wavelength range of 500-800 nm, excitation slit width set to 10 nm, and emission slit width set to 10 nm. A baseline scan of SapB-RP was performed and then 10, 5 µL injections from the experimental stock of A2E were made, with a scan performed after each injection for a total of 11 scans.

Fluorescence Binding of SapB to Atovaquone (ATO) and Blocking of A2E Binding

Experimental Details

Lyophilized SapB was re-suspended in pH 5.5 50 mM phosphate buffer to create a SapB stock. The concentration of the stock solution was determined to be 0.28435 mM via uv-vis absorbance at 278 nm with an extinction coefficient of 2920 $M^{-1}cm^{-1}$. For the fluorescence binding study, the stock was diluted in pH 5.5 50 mM phosphate buffer to reach a final concentration of 40 µM SapB in 1 mL of pH 5.5 50 mM phosphate buffer.

A primary ATO stock of 1.1 mM in DMSO was used for these experiments. The concentration of the ATO stock was confirmed via uv-vis absorbance at 253 nm with an extinction coefficient of 27300 $M^{-1}cm^{-1}$.

A purified A2E stock in 1 mL DMSO was determined to have a concentration of 1.1 mM via uv-vis at 436 nm with an extinction coefficient of 36900 $M^{-1}cm^{-1}$. This stock solution was then used to make another stock with a final concentration of 92.8 µM in 1 mL DMSO, confirmed again via uv-vis.

TABLE 2

Summary of Analyte Concentrations and Conditions for SapB-ATO + A2E Block

| Analyte | Primary Stock Conc. | Experimental Stock Conc. |
|---|---|---|
| Saposin B | 0.28435 mM | 0.040 mM |
| ATO | 1.1 mM | 0.0216 mM |
| A2E | 1.1 mM | 0.0928 mM |

A SapB-ATO complex was formed by adding 20 µL of the experimental stock to 1 mL of the SapB experimental stock for a final volume of 1020 µL in a 1.5 mL Eppendorf tube. The solution was gently rotated at room temperature, in foil, for 15 minutes. The entire 1020 µL was then transferred to a clear fluorescence cuvette. Fluorescence experiments were performed under emission conditions on a Cary Eclipse Fluorescence Spectrophotometer, with an excitation wavelength of 444 nm, emission wavelength range of 500-800 nm, excitation slit width set to 10 nm, and emission slit width set to 10 nm. A baseline scan of SapB-ATO was performed and then 15, 2 µL injections from the experimental stock of A2E were made, with a scan performed after each injection for a total of 16 scans.

Example 2—Lysosomal Saposin B Binds the Lipofuscin Bisretinoid A2E and Prevents its Enzymatic and Photo Degradation Materials and Methods A2E and SapB were prepared and purified according to literature reports. All sapB protein solutions in this study were prepared in 50 mM phosphate buffer, pH 5.5. Protein concentration was determined spectrophotometrically using a molar absorptivity value of 2950 $M^{-1}cm^{-1}$ at 280 nm. A2E solutions were prepared in DMSO and their concentration determined using molar absorptivity values of 25600 $M^{-1}cm^{-1}$ at 330 nm or 36900 $M^{-1}cm^{-1}$ at 440 nm.

Fluorescence Spectroscopy

Fluorescence quenching measurements were performed on a Varian Cary Eclipse fluorimeter equipped with a QNW Peltier temperature controller. The experiments were conducted at 25.00±0.01° C. in 50 mM phosphate buffer, pH 5.50 or 7.40 using 278 nm excitation wavelength for sapB emission spectra at 325 nm (FIG. 2) or 444 nm excitation for A2E emission at 602 nm (FIG. 3) with excitation and emission monochromators bandwidth of 5 nm each. The fluorescence quenching data were analyzed using OriginLab software version 8.

Ultra-Violet and Visible Spectroscopy

Conventional ultraviolet visible spectroscopy was performed on a Varian Cary 50 Bio spectrophotometer from Agilent Technologies. The stock solutions of various reagents were prepared as follow: HRP in DI water, A2E in DMSO, SapB in 50 mM phosphate buffer, pH 5.5, CoQ10 in THF (tetrahydrofurane) and 3% $H_2O_2$ solution diluted in DI water from an initial stock at 30%. The 340 nm kinetic experiments were monitored every 5 minutes for a total of 400 min following the sequential addition of all reagents as indicated in FIG. 4. The HRP solution of FIG. 5 was prepared in 20 mM phosphate buffer, 1% tween, pH 5.5, 25° C. All concentrations given in the figure caption are final concentrations following mixing of the reagents. The spectrophotometric data were further analyzed with OriginLab software version 8.

Protein-Protein Interaction and SapB-HRP Complex Formation.

Figure 7:
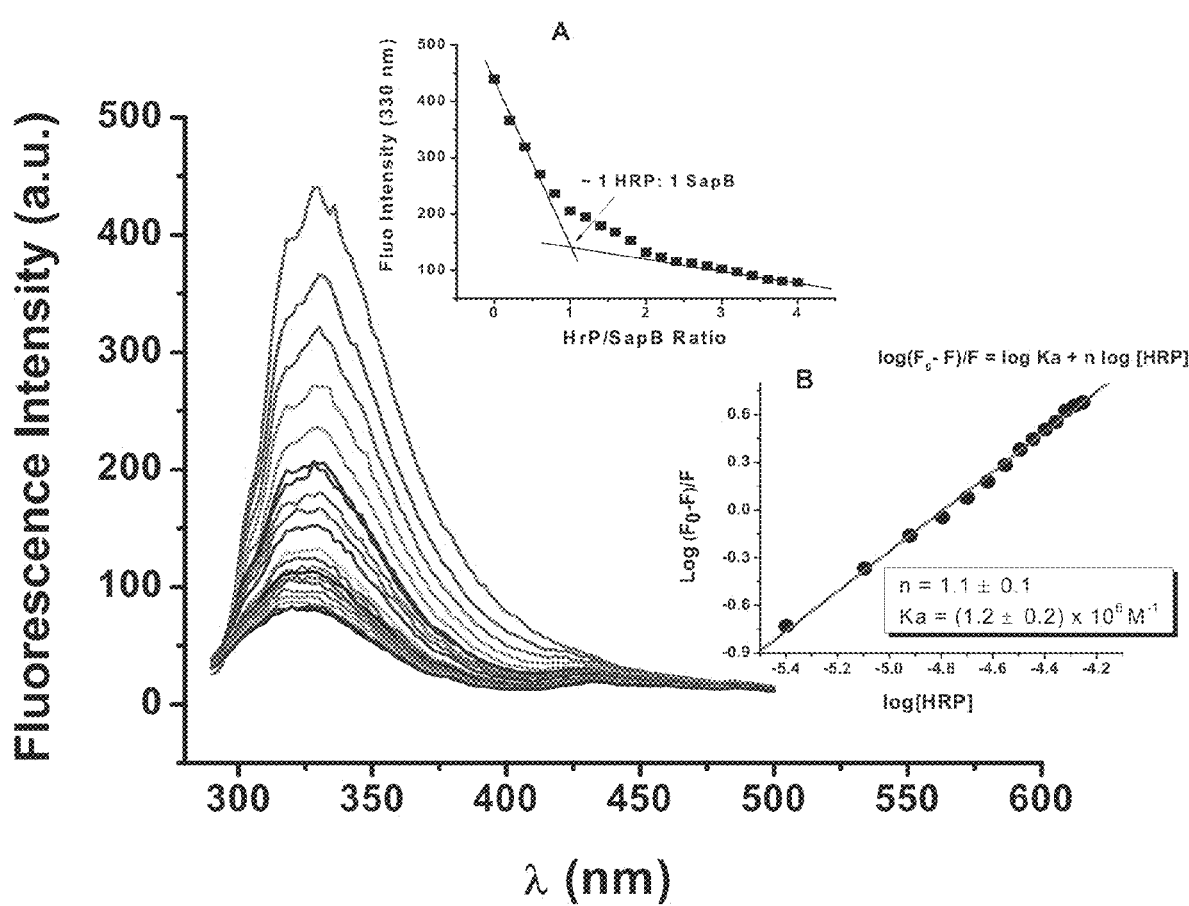
FIG. 7. Change in the fluorescence emission spectra of SapB in the presence of various amounts of HRP. Inset A shows the plot of the fluorescence intensity vs. the HRP/SapB mole ratio and inset B shows a double logarithmic plot of HRP quenching effect on the fluorescence of SapB. Conditions: 20 µM SapB, 2 µL injections of 1.5 mM HRP (0.2 HRP/SapB per injection), 50 mM phosphate buffer, pH 5.5 and 25° C.
Figure 8:
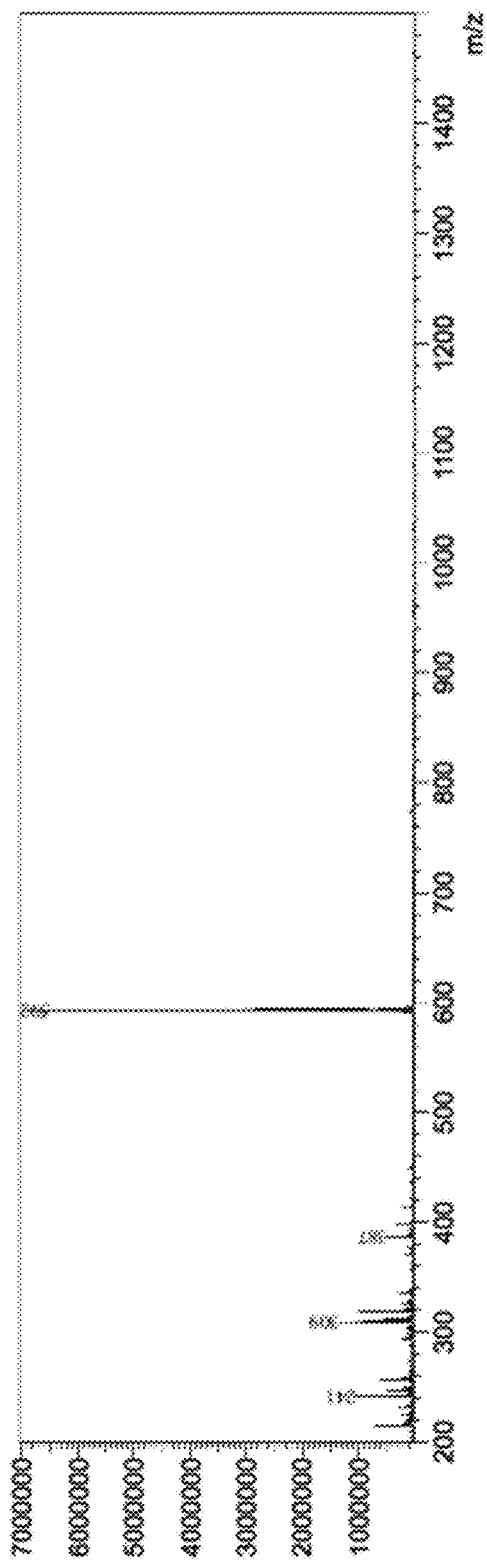
FIG. 8. Starting A2E stock (1.9 mM; 100% DMSO) diluted 1:1000 into methanol for electrospray mass spectrometry. Expected mass of A2E 592 m/z.
Figure 9:
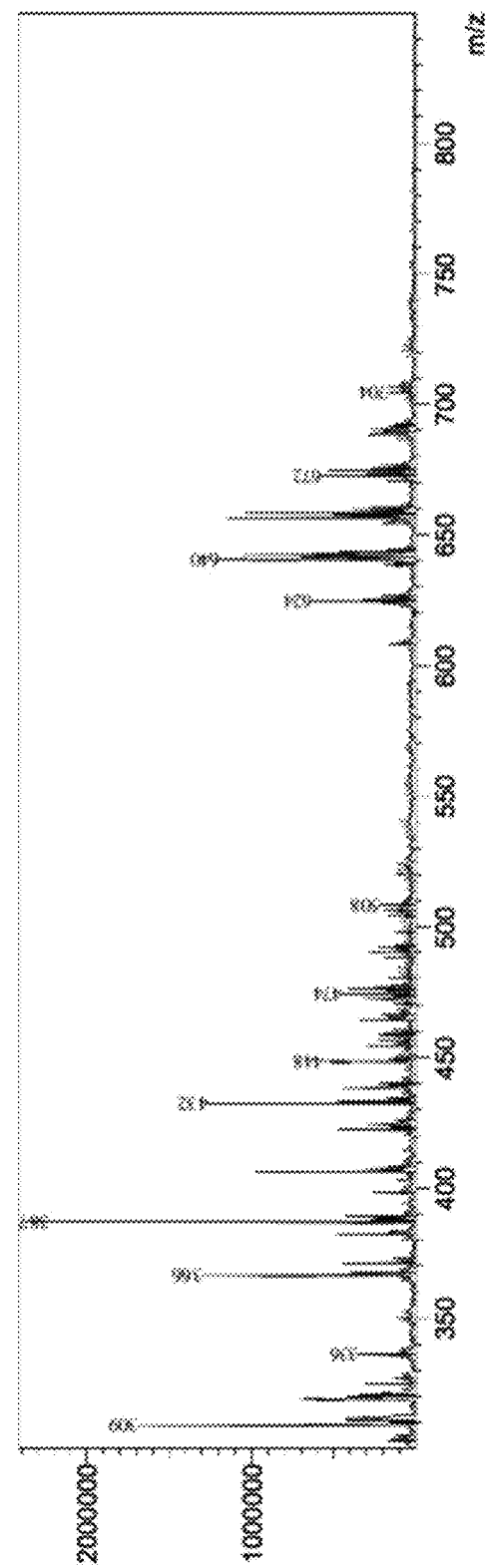
FIG. 9. A2E (1% Methanol in 50 mM Phosphate) after exposure to blue light (sample diluted in methanol 1:1000 for MS analysis). Note presence of A2E-2ox (624 m/z), A2E-3ox (640 m/z), A2E-4ox (656 m/z), A2E-5ox (672 m/z), A2E-6ox (688 m/z), A2E-7ox A2E-8ox (704 m/z) A2E-9ox (722 m/z).
Figure 10:
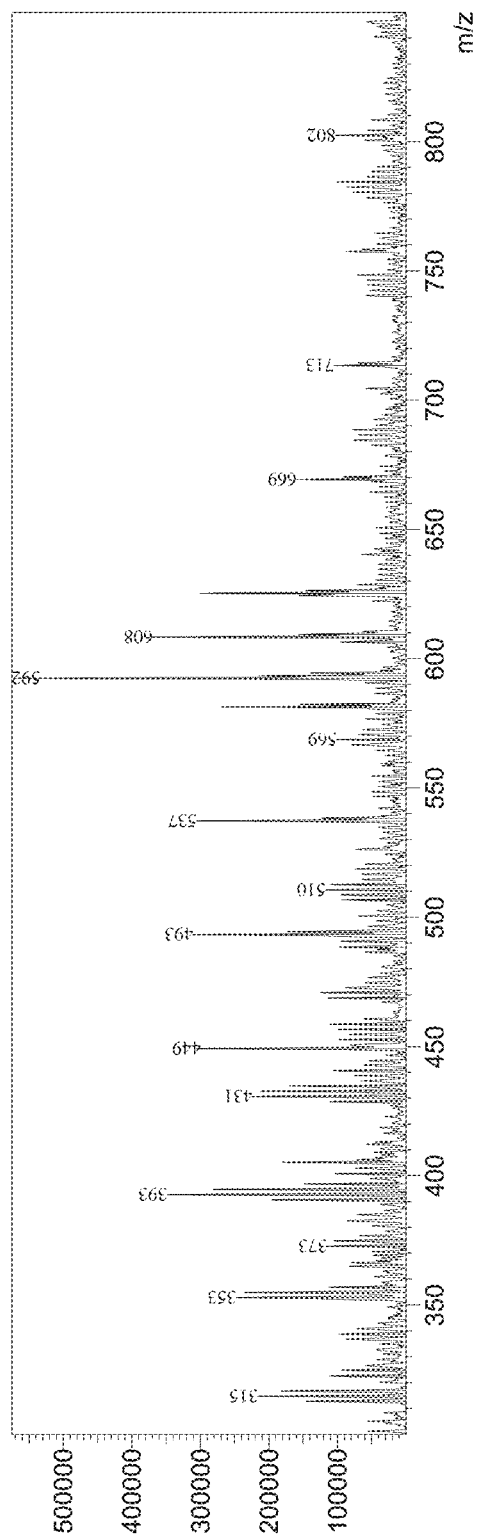
FIG. 10. A2E (1% DMSO in 50 mM Phosphate) after exposure to blue light (sample diluted in methanol 1:1000 for MS analysis). Note presence of A2E (592 mx) and oxidized products A2E-ox (608 m/z), A2E-2ox (624 m/z).

To examine the possibility of a protein-protein interaction between HRP and SapB, the intrinsic fluorescence of SapB was monitored at 330 nm following addition of small increments of HRP. FIG. 7 shows significant quenching of the fluorescence emission spectra of SapB with increasing HRP concentrations, suggesting binding and substantial alteration in the local environment of aromatic moieties in or around the proteins' binding sites (SapB contains two tyrosine and two phenylalanine). The double logarithmic plot $$\left(\text{i.e. } \log\frac{(F_0 - F)}{F} \text{ versus } \log[Q]\right)$$

and titration curves (insets A and B of FIG. 5) indicate a binding stoichiometry of ~1 HRP per SapB monomer. While the nature of this association may involve a combination of hydrophobic contacts, van der Waals forces, and/or salt bridges, this protein-protein transient interaction is rather strong, having a binding affinity around $1 \times 10^6$ $M^{-1}$.

Blue Light Degradation

In order to further examine the protective effects of sapB towards A2E in terms of photooxidation, additional ultraviolet spectroscopy was performed on a Varian Cary 50B Spectrophotomer. The stock solutions were prepared as follows: SapB in 50 mM phosphate buffer, pH 5.5 and A2E in 100% methanol or 100% DMSO. The samples were exposed to blue light in five-minute increments and monitored after each exposure for a total of 30 min. The data was further analyzed with OriginLab software version 8. The final product was examined via mass spectroscopy to identify products as a result of blue light exposure. Evidence for photooxidized species are clearly indicated.

Example 3—Identification of Second Binding Site

The interaction of SapB (prepared as described above) with a variety of ligands was followed by monitoring the quenching of the fluorescence intensities of the protein's tyrosine residues upon binding (FIG. 12 Panels a-f). An excitation wavelength of 278 nm was used and the fluorescence emission was monitored between 285 and 500 nm.

For each ligand tested 40 µM SapB in 50 mM phosphate buffer at pH 5.5 was titrated with ligand and quenching was monitored at the fluorescence maxima at 330 nm. Quenching, coupled with no observed spectral shift, was interpreted to mean that the local tyrosine residue environment was not altered upon interaction with the ligand. All of the fluorescence data were analyzed by a double logarithmic Stern-Volmer plot, shown for all ligands, using the emission maxima to determine binding affinity, presented in Table 3, and using the following equation $$\log\frac{(F_0 - F)}{F} = n\log[Q] + \log K_A$$

Figure 17:
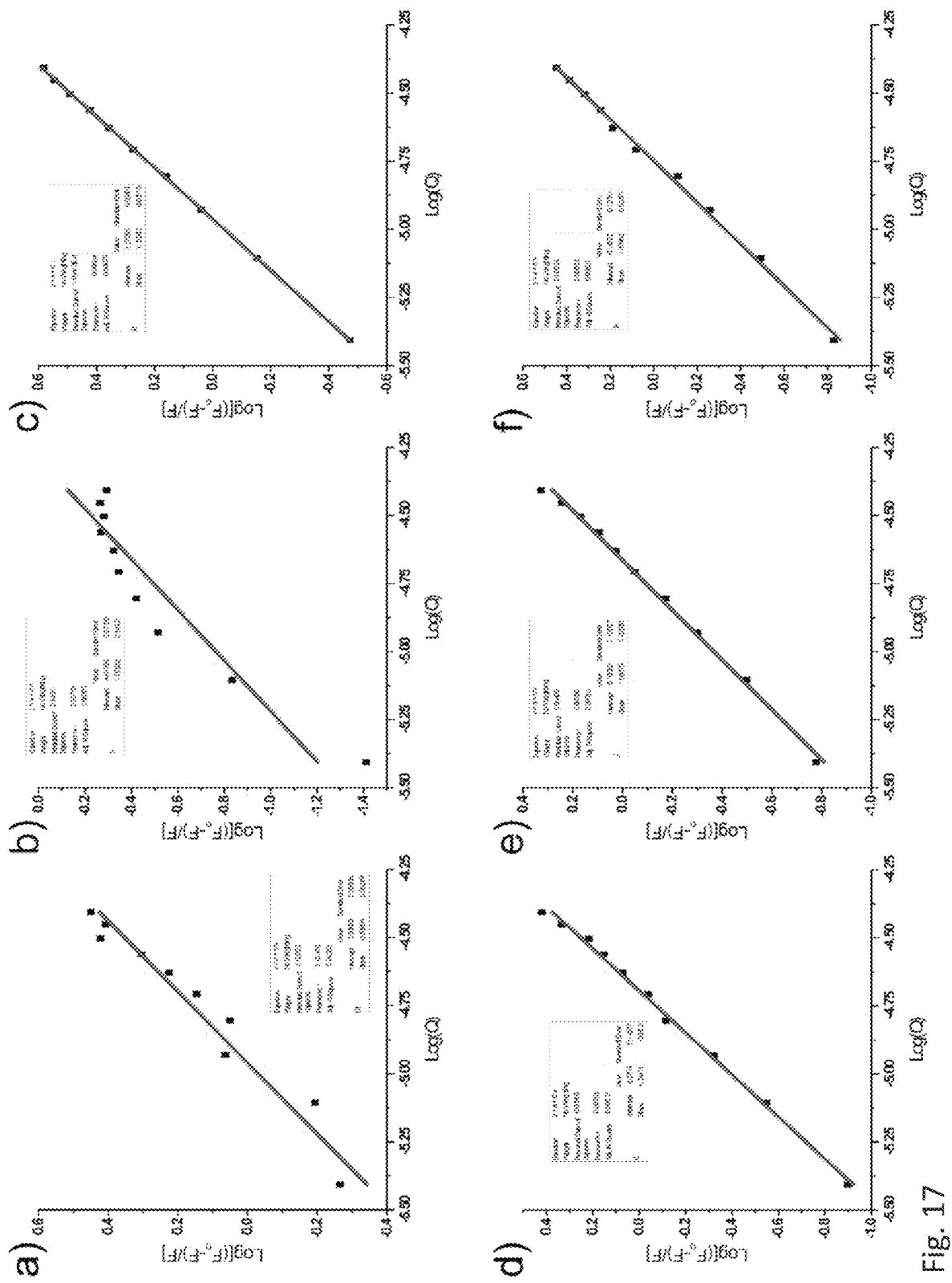
FIG. 17. Double Logarithmic Stern-Volmer Plots for Spectrophotometric Titrations of SapB with Ligand. Fluorescence quenching was monitored at the maximum fluorescence of SapB at 330 nm, relative to increasing concentration of quenching ligand. Panel a) HCQ, Panel b) ACar, Panel c) PEth, Panel d) PCho, Panel e) CoQ4, Panel f) CoQ9 Conditions: 40 µM SapB in 50 mM phosphate buffer pH 5.5 with 2 µL injections of 2 mM ligand (50 mM phosphate buffer, pH 5.5 for HCQ; all others in 100% DMF) conducted at room temperature.
Figure 18:
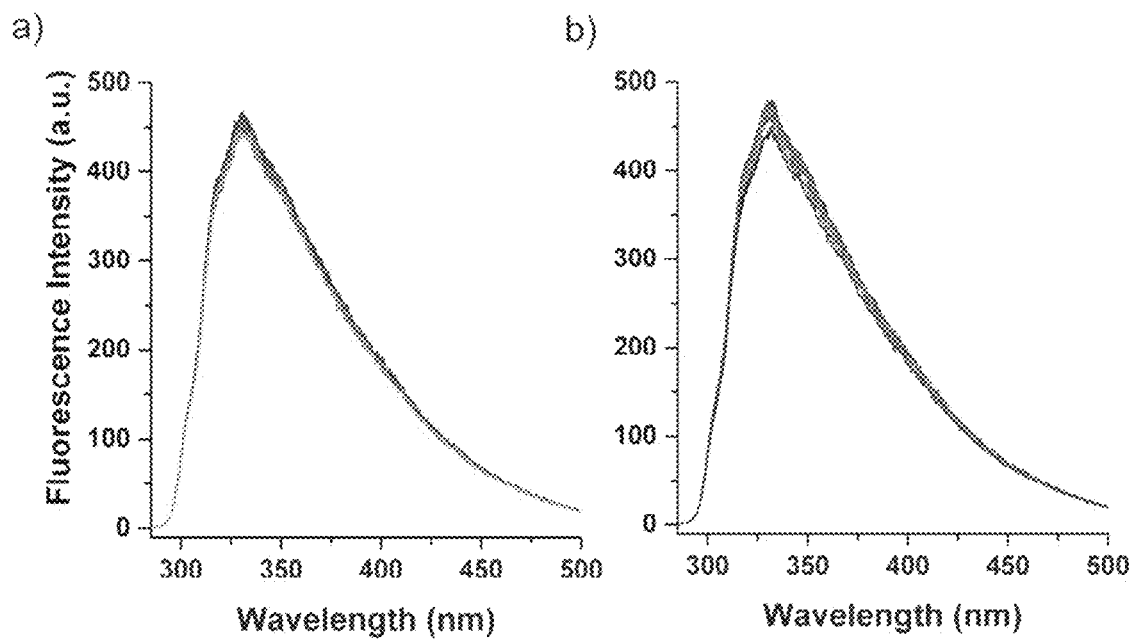
FIG. 18. Panel a) 40 µM SapB in a solution of 50 mM phosphate buffer at pH 5.5, followed by addition of 20×2 µL injections of 50 mM phosphate buffer at pH 5.5. Panel b) 40 µM SapB in a solution of 50 mM phosphate buffer at pH 5.5, followed by direct titration of 20, 2 µL injections of 100% DMF.

(see also FIG. 17 Panels a-f).

Figure 13:
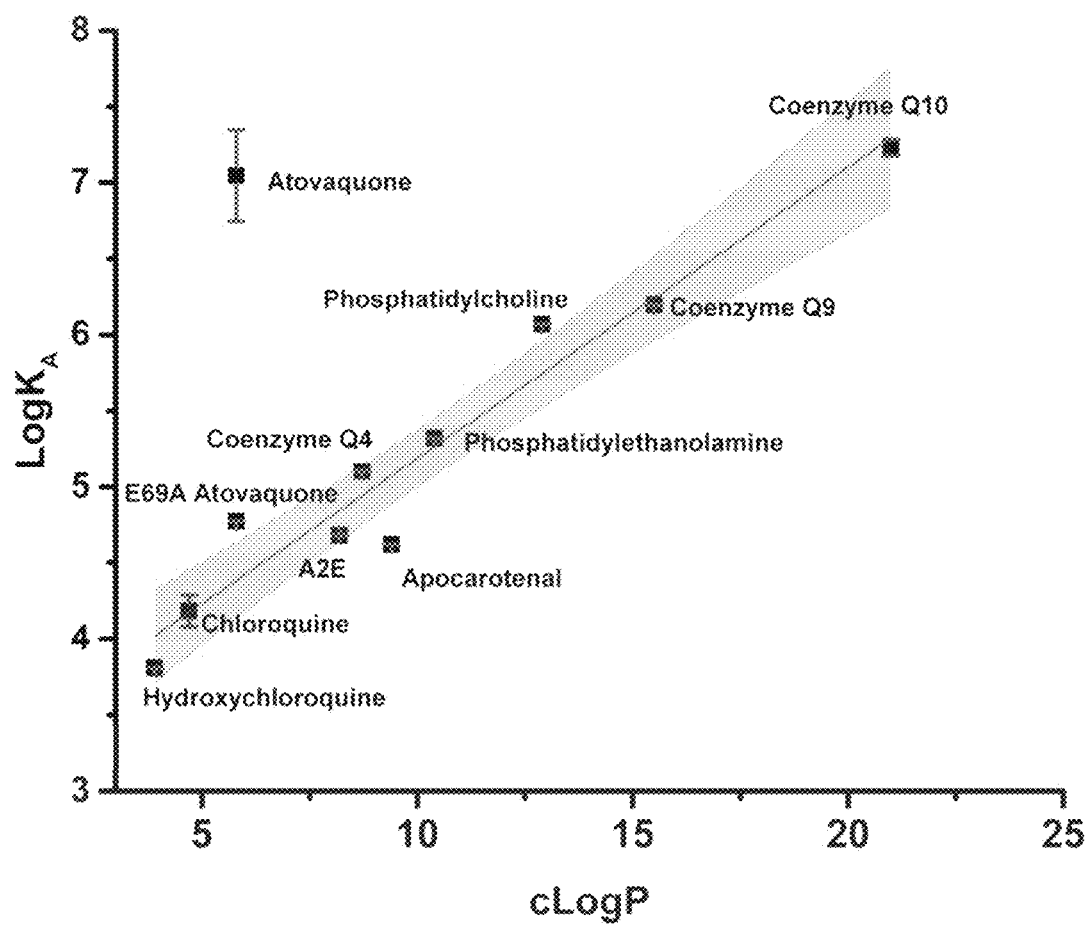
FIG. 13. A plot of ligand Log $K_A$ of binding by SapB vs. ligand calculated c Log P at pH 5.5. Each ligand binding experiment was per-formed in triplicate and each point represents the average of the three runs. The best fit line was plotted using a linear least squares regression, excluding the ATO data point. The best-fit line has a calculated R$^2$ value of 0.934 with an intercept of 3.28 and a standard error of 0.190, and a slope of 0.191 with a standard error of 0.017. The shaded area denotes the upper and lower 95% confidence intervals.

Upon collection of all ligand binding affinities it became clear that with increasing hydrophobicity of the ligand, the $K_A$ with SapB increases. This is consistent with the known primary function of SapB as an activator and binder of lipids in the lysosome. Interestingly, a plot of Log $K_A$ vs. cLogP (see FIG. 13) shows a clear linear trend with strong correlation (here defined as having an $R^2$ value greater than 0.9), with only [SapB-ATO]$_{complex}$ deviating substantially from the line for those ligands tested, suggesting that [SapB-Ligand]$_{complex}$ formation is driven primarily through entropic factors.

TABLE 3

Ligand LogK$_A$ of binding by SapB vs. Ligand calculated cLogP

| Ligand | LogK$_A$ | cLogP[a] |
|---|---|---|
| Hydoxychloroquine | 3.809 | 3.90 |
| Chloroquine | 4.154 | 4.70 |
| Atovaquone | 7.540 | 5.80 |
| A2E | 4.680 | 8.20 |
| Coenzyme Q$_4$ | 5.103 | 8.72 |
| Apocarotenal | 4.618 | 9.40 |
| Phosphatidylethanolamine | 5.227 | 10.4 |
| Phosphatidylcholine | 6.075 | 12.9 |
| Coenzyme Q$_9$ | 6.196 | 15.5 |
| Coenzyme Q$_{10}$ | 7.200 | 21.0 |

[a]cLogP values were obtained using the ACD/LogP method.

The deviation observed for [SapB-ATO]$_{complex}$ from the trend warranted further investigation. In order to examine this deviation, a previously described SapB mutant E69A (denoted as E69A from here on) was used. Fluorescence studies were performed with E69A and ATO as described herein for wild type SapB. Stern-Volmer analysis showed a three order of magnitude decrease in $K_A$, from ~$10^7$ for [SapB-ATO]$_{complex}$, to ~$10^4$ for [E69A-ATO]$_{complex}$, suggesting considerable disruption of binding with a single (E to A) amino acid change.

Figure 14:
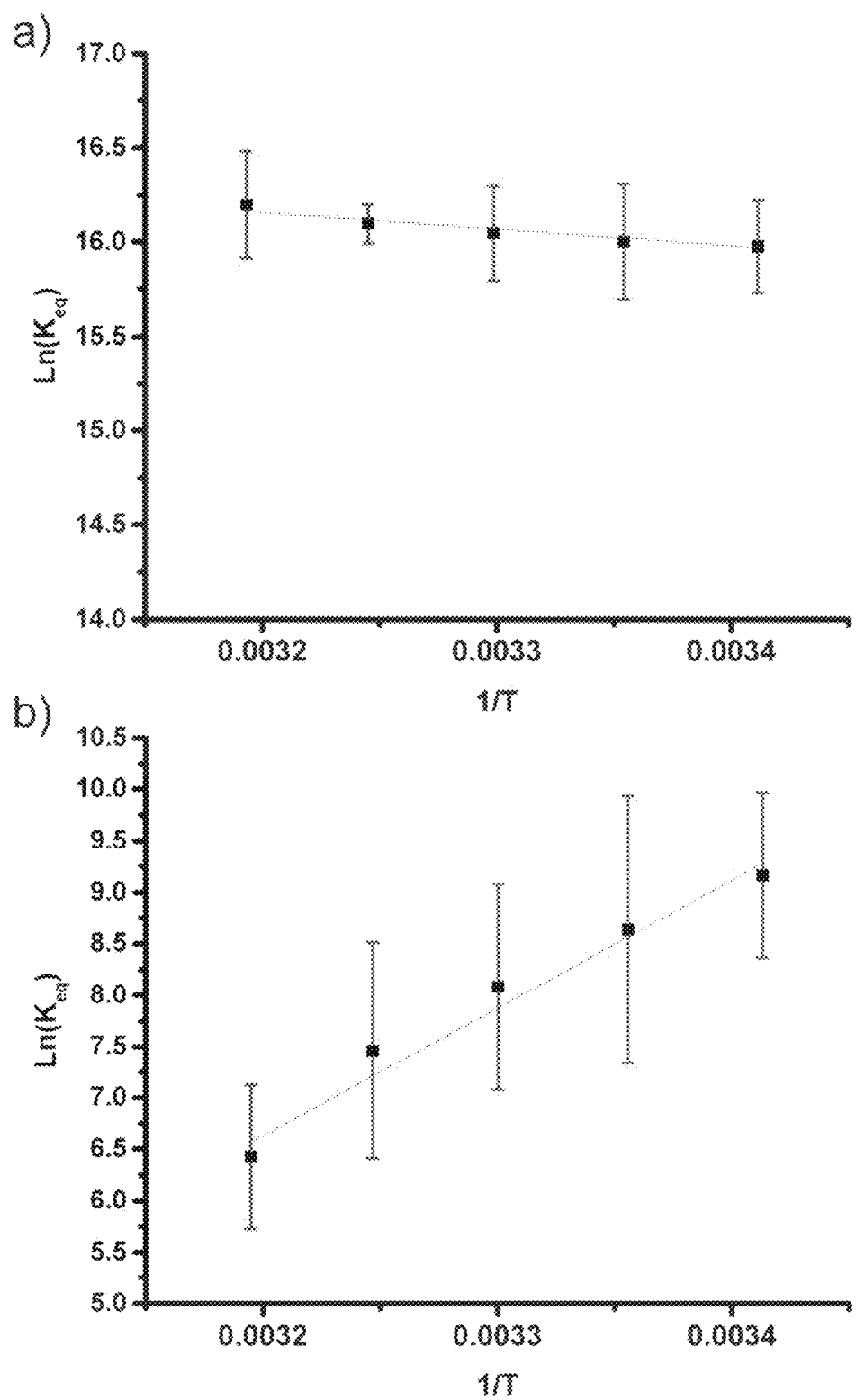
FIG. 14. Panel a) Determination of SapB-ATO enthalpy of binding via temperature dependent fluorescence binding assay. Panel b) Determination of E69A-ATO enthalpy of binding via temperature dependent fluorescence binding assay. Data was plotted in accordance with the standard equation provided in Example 3, and the calculated thermodynamic parameters are presented in Table 4.

Isothermal titration calorimetry has shown that [SapB-ATO]$_{complex}$ formation has a larger enthalpic contribution than [SapB-CQ]$_{complex}$ and [SapB-CoQ$_{10}$]$_{complex}$. Thus, the shift in binding affinity between [SapB-ATO]$_{complex}$ and [E69A-ATO]$_{complex}$ binding may be due to a shift in the thermodynamics of binding. In order to test this, temperature dependent fluorescence studies were performed with E69A and ATO, as well as with SapB and ATO. Fluorescence titration experiments were carried out at five different temperatures for each of the E69A-ATO and SapB-ATO experiments (FIG. 14). At each temperature, protein was prepared in phosphate buffer solution and ATO was then added via titration. The quenching of SapB or E69A fluorescence was monitored at 330 nm and the $K_A$ was calculated via double logarithmic Stern-Volmer analysis. The best-fit plot of $lnK_{eq}$ vs. 1/T, where was used to calculate the standard enthalpy, entropy, and Gibb's Free energy of binding for the formation of [E69A-ATO]$_{complex}$ and $$[SapB\text{-}ATO]_{complex}\left(l.n.\ K_{eq} = \frac{-\Delta H^\circ}{RT} + \frac{\Delta S^\circ}{R}\right).$$

Figure 19:
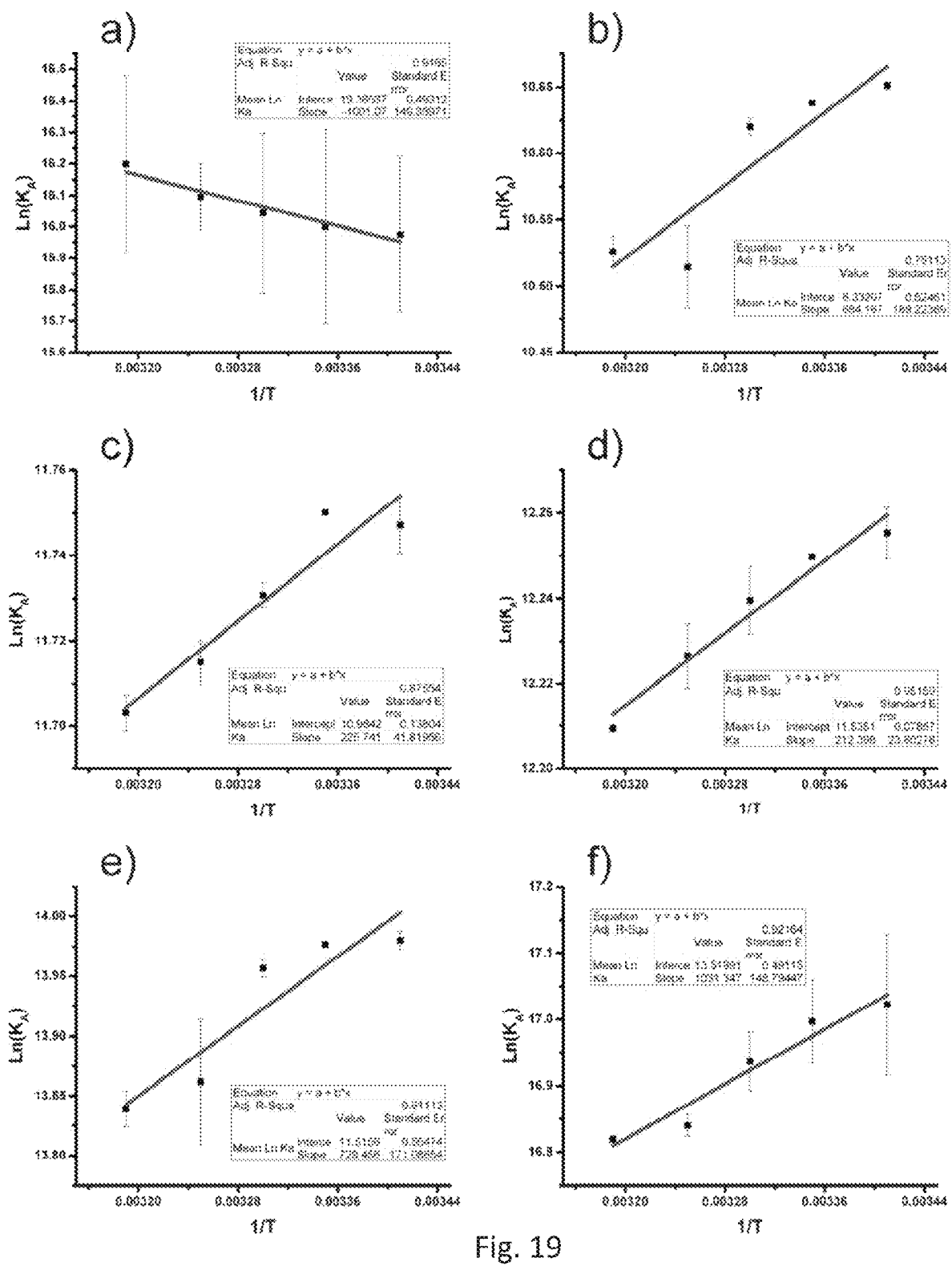
FIG. 19. Van't Hoff plots for the interactions of SapB with Panel a) ATO Panel b) CQ Panel c) CoQ$_4$ $_{Panel}$ d) PEth Panel e) PCho Panel f) CoQ$_{10}$.

The standard enthalpy for [E69A-ATO]$_{complex}$ formation was calculated to be −103.5±8.966 kJ K$^{-1}$mol$^{-1}$ and for [SapB-ATO]$_{complex}$ formation it was calculated to be 7.249±1.163 kJ K$^{-1}$mol$^{-1}$, indicating that a single amino acid mutation resulted in a shift in the sign of standard enthalpy from negative to positive. Other calculated thermodynamic parameters are presented in Table 4. The shift in the standard enthalpy supports a hypothesis that [SapB-ATO]$_{complex}$ formation differs from other [SapB-Ligand]$_{complexes}$ by being driven via an enthalpic contribution. Thermodynamic parameters were also calculated for other ligands (see FIG. 19)

Figure 15:
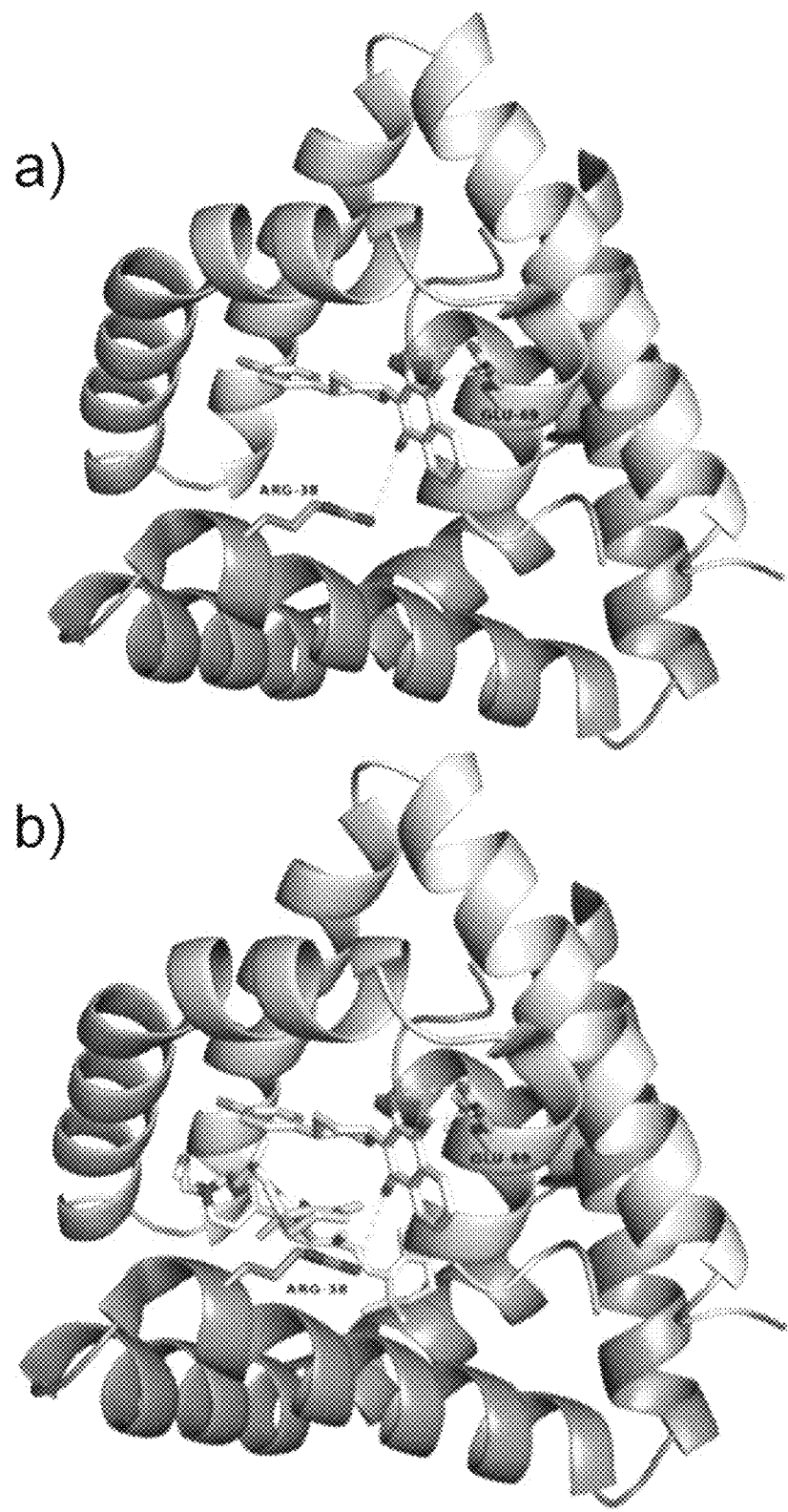
FIG. 15. Panel a) Model of [SapB-ATO]complex. Hydrogen bonds between ATO and SapB are noted at residues E69 and R38. Panel b) Model of [SapB-ATO-A2E]complex FIG. 16. Depicting various ligands of FIG. 11 and the Saposin B structure.
Figure 16:
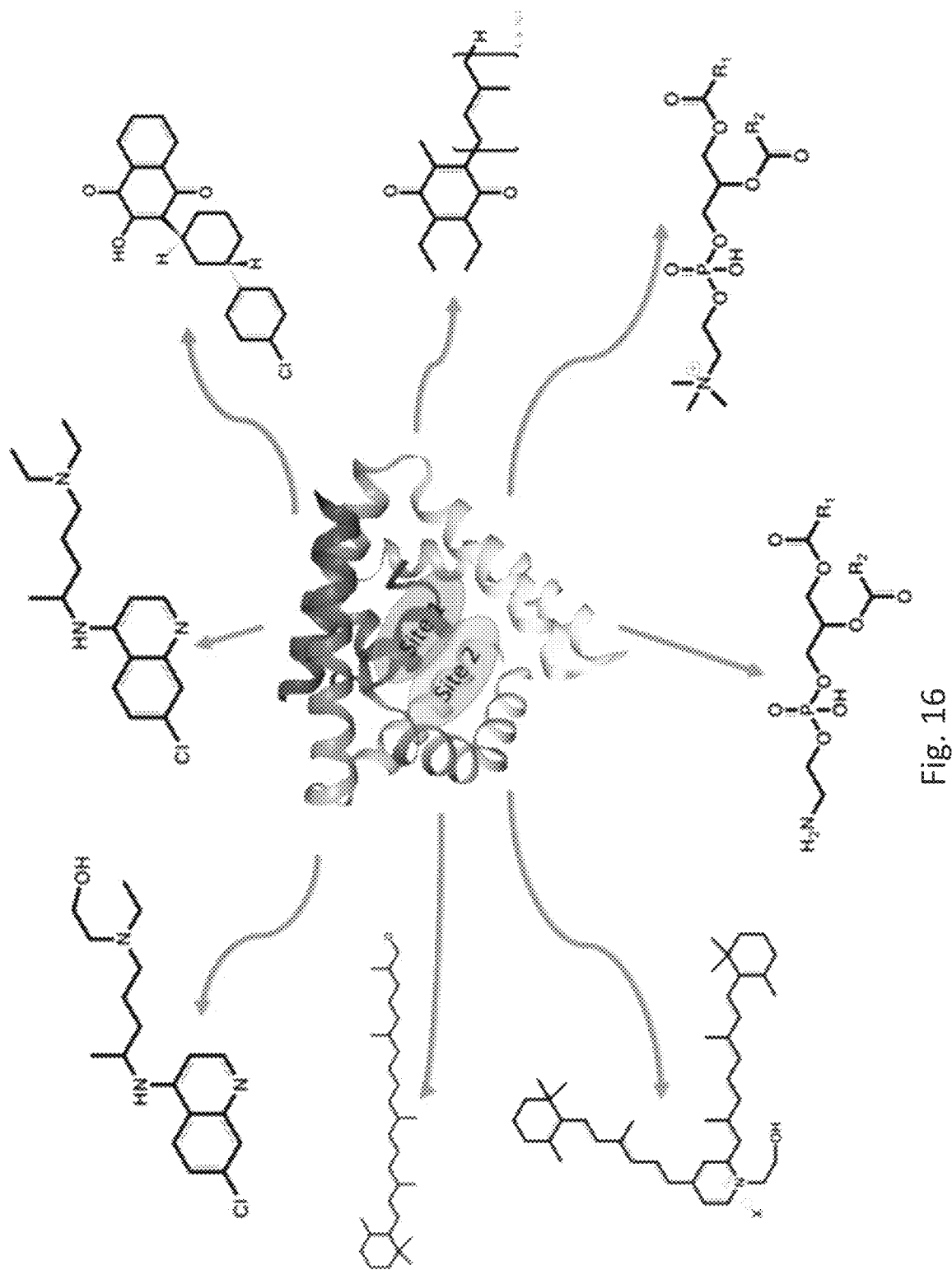

Computational docking studies were used to further examine the decrease in binding affinity between native SapB and E69A. A change in orientation between ATO and the SapB or E69A in the binding pocket may be responsible for this shift. Docking of ATO was performed with Swiss-Dock using the structure of [SapB-CQ]$_{complex}$ (PDB 4V2O) as a model. The orientation of the ATO ligand was checked manually using Coot and optimized for putative hydrogen bonding interactions. The resulting computations showed three putative hydrogen bonds within the [SapB-ATO]$_{complex}$ (FIG. 15 Panel a) at E69 and arginine residue 38 (R38), and the disruption of all three bonds in the [E69A-ATO]$_{complex}$. These results suggest that the decreased affinity may be due to disrupted enthalpic contributions via the elimination of three hydrogen bonds and supports the calculated enthalpy values.

TABLE 4

Calculated thermodynamic parameters for SapB-ATO binding and E69A-ATO binding.

| Caculated Parameters | SapB-ATO | E69A-ATO |
|---|---|---|
| $K_A$ (M$^{-1}$) at 25° C. | (0.891 ± 0.255) × 10$^7$ | (1.71 ± 1.08) × 10$^4$ |
| $\Delta H^\circ$ (kJ K$^{-1}$ mol$^{-1}$) | 7.249 ± 1.163 | −103.5 ± 8.966 |
| $\Delta G^\circ$ (kJ mol$^{-1}$) | −46.96 ± 1.170 | 82.33 ± 8.794 |
| $\Delta S^\circ$ (J K$^{-1}$ mol$^{-1}$) | 157.51 ± 3.926 | −276.1 ± 29.52 |

The previously published crystal structures of SapB and [SapB-CQ]$_{complex}$ shows a v-shaped, hydrophobic pocket suitable for lipid and/or small molecule binding. However, solution structure NMR studies have proven challenging, and molecular dynamics modeling show the SapB dimer is inherently flexible. Additional work has also shown that this dimeric flexibility plays a role in overall SapB function, and mutants with more rigidity led to a decline in function. This suggests that a mechanism underlying the broad binding specificity of SapB reported herein, and its ability to bind a variety of hydrophobic molecules, may be due to an inherent conformational flexibility.

In order to probe the adaptability of the pocket and its ability to accept multiple ligands, we conducted 'order of addition' fluorescence binding experiments using pre-formed [SapB-Ligand]$_{complexes}$, followed with direct titration of a second ligand (Ligand=ATO or A2E).

Figure 20:
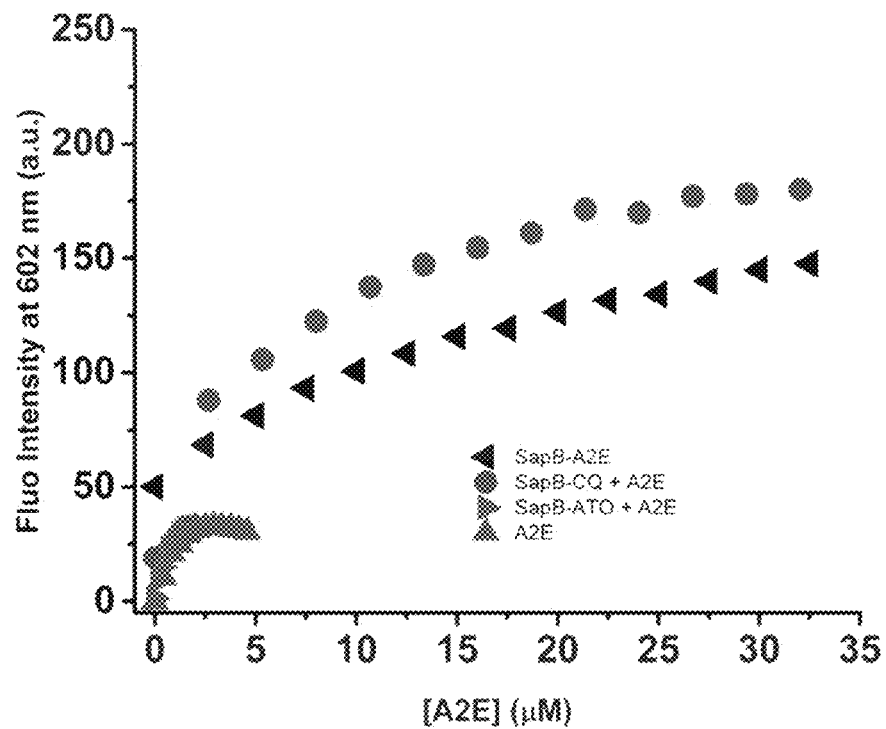
FIG. 20. Spectrophotometric titration of pre-formed [SapB-Ligand] complex with A2E. Conditions: 40 µM SapB and 20 µM Ligand was pre-complexed in 50 mM phosphate buffer, pH 5.5. [SapB-Ligand]$_{complex}$ was then titrated with 2 µL injections of 1 mM A2E, and the fluorescence emission spectrum was collected between 500-800 nm, with an excitation at 444 nm, and the maximum fluorescence of A2E was observed at 602 nm. The red curve represents multiple incremental additions of A2E to buffer alone, in the absence of SapB.
Figure 21:
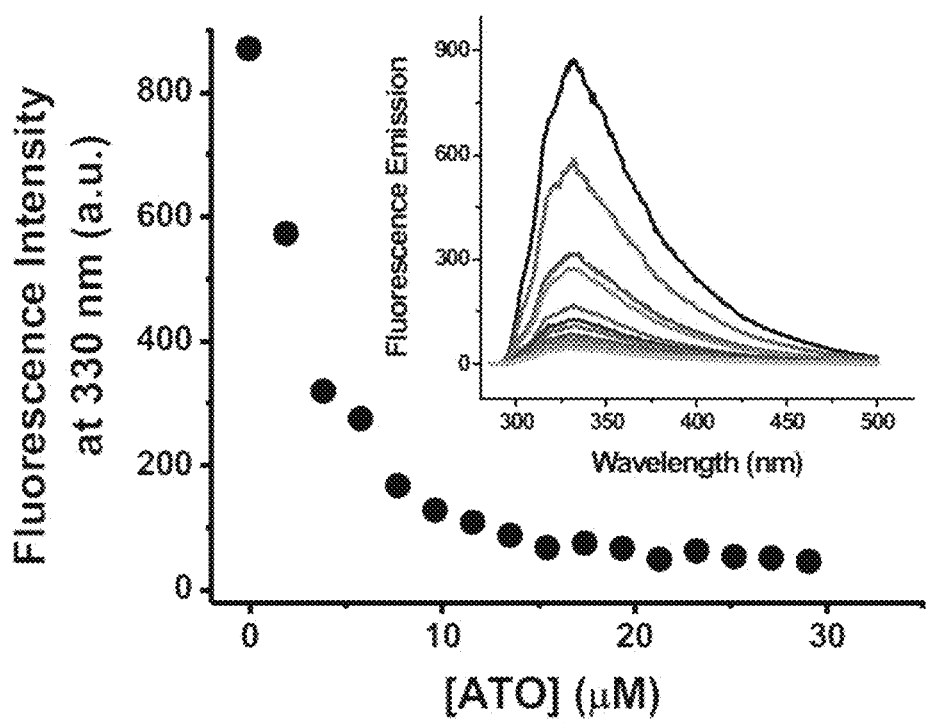
FIG. 21. Spectrophotometric titration of pre-formed [SapB-A2E]$_{complex}$ with ATO. Conditions: 40 µM SapB and 20 µM A2E was pre-complexed in 50 mM phosphate buffer, pH 5.5. The [SapB-A2E]$_{complex}$ was then titrated with 2 µL injections of 1 mM ATO and the fluorescence emission spectra were collected between 285-500 nm using $\lambda_{ex}$=278 nm and $\lambda_{em}$=300 nm.

Titration of A2E into a pre-formed solution of [SapB-ATO]$_{complex}$ resulted in no A2E binding, as shown by fluorescence saturation point of A2E observed and compared to that of SapB binding of A2E alone (see FIG. 20). This lack of A2E binding indicates that the pre-formed [SapB-ATO]$_{complex}$ has a blocking effect, consistent with calculations that support ATO is more surface bound, rather than 'buried' inside the SapB hydrophobic pocket. However, forming [SapB-A2E]$_{complex}$ first and then following it with titration of ATO, resulted in clear ATO binding (FIG. 21). Further analysis shows, while the dimer cannot accommodate two ATO molecules at the same time (due to the dimer asymmetry produced upon binding and the more surface bound nature of such binding) (FIG. 15 Panel a), the dimer is able to accept A2E and ATO simultaneously (FIG. 15 Panel b), due to the fact that A2E is 'buried' deeper into the SapB dimer hydrophobic cavity.

These studies demonstrate that SapB will bind a broad range of ligands and that such binding can be predicted based upon the ligand's c Log P. The results also demonstrate that SapB can accommodate multiple ligands simultaneously (with order of binding and site of binding important for such), in large part due to the conformational flexibility described by Kessler and Sansom.

Materials and Methods

Materials and Methods—Saposin B (SapB) was prepared and purified as described above. Briefly, SapB solutions in this study were prepared in 50 mM phosphate buffer, pH 5.5. Protein concentration was determined spectrophotometrically using a molar absorptivity value of 2950 M$^{-1}$ cm$^{-1}$ at 280 nm. Ligand solutions were prepared in 100% dimethylformamide (DMF) to a concentration of 2 mM, with the exception of hydoxychloroquine (HCQ), which was prepared in 50 mM phosphate buffer, pH 5.5. The concentrations of all the ligands were determined via ultraviolet-visible spectroscopy using molar absorptivity values of: 36 900 M$^{-1}$ cm$^{-1}$ at 440 nm for A2E; 7500 M$^{-1}$ cm$^{-1}$ at 331 nm for CQ; 226.9 M$^{-1}$ cm$^{-1}$ at 329 for HCQ; 27 300 M$^{-1}$ cm$^{-1}$ at 253 nm for ATO; 22 540 $M^{-1}$ $cm^{-1}$ at 279 nm for PEth; 27 500 $M^{-1}$ $cm^{-1}$ at 280 nm for PCho; 4150 $M^{-1}$ $cm^{-1}$ at 283 for CoQ4; and 3750 $M^{-1}$ $cm^{-1}$ at 282 nm for CoQ9. 4.2. Fluorescence Spectroscopy. Fluorescence quenching measurements were performed on a Varian Cary Eclipse fluorimeter equipped with a QNW Peltier temperature controller. The binding experiments were conducted at 25.00±0.01° C. in 50 mM phosphate buffer, pH 5.5, using 278 nm excitation wavelength for SapB emission spectra at 330 nm (FIG. 1a-f) with excitation and emission monochromators bandwidth of 5 nm each. Temperature sensitive binding experiments were performed between 20.00±0.01 and 40.00±0.01° C. using 278 nm excitation wavelength for SapB emission spectra at 331 nm, with excitation and emission monochromators bandwidth of 5 nm each. The fluorescence quenching data were analyzed using OriginLab software version 8.

Docking studies were performed with SwissDock using the structure of SapB-CQ (PDB 4V2O) as a model. The orientation of the ATO ligand was checked manually using Coot and optimized for putative hydrogen bonding interactions.

Accurate determination of SapB-Ligand binding affinity via titration fluorescence spectroscopy is reliant on protein fluorescence quenching being due to protein-ligand interaction, and not a consequence of added solvent into the system. The majority of the ligands tested here were dissolved in DMF before being added to the SapB protein, buffer solution, so any quenching of SapB fluorescence by DMF would have skewed our results. Supplemental FIG. 2 shows that addition of up to 40 µL phosphate buffer or 100% DMF, to a protein solution had virtually no effect on SapB fluorescence, suggesting that the observed fluorescence quenching of SapB is solely due to SapB-ligand interactions without any measurable effect from the solvents.

Order of Addition Fluorescence Binding

In order to examine the flexibility and ability of the SapB binding pocket to accommodate the binding of multiple ligands, we prepared multiple [SapB-Ligand]complexes and followed it with direct titration of A2E. The change in A2E's fluorescence maxima was determined to indicate whether or not A2E was able to bind to the preformed [SapB-Ligand] complex. The resulting experiments indicated that [SapB-ATO]complex was able to block A2E binding, and addition of A2E to [SapB-ATO]complex was comparable to A2E titration directly into 50 mM phosphate buffer at pH 5.5 in the absence of SapB.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

Although the present disclosure has been described with a certain degree of particularity, it is understood the disclosure has been made by way of example, and changes in detail or structure may be made without departing from the spirit of the disclosure as defined in the appended claims.

All references disclosed herein and below, whether patent or non-patent, are hereby incorporated by reference as if each was included at its citation, in its entirety. In case of conflict between reference and specification, the present specification, including definitions, will control.

REFERENCES

Kiser, P. D.; Palczewski, K. Annu. Rev. Vis. Sci. 2016, 2, 197-234.
Jarrett, S. G.; Boulton, M. E. Mol. Asp. Med. 2012, 33, 399-417.
Sparrow, J. R. Proc. Natl. Acad. Sci. U.S.A. 2016, 113, 4564-4569.
Ueda, K.; Zhao, J.; Kim, H. J.; Sparrow, J. R. Proc. Natl. Acad. Sci. U.S.A. 2016, 113, 6904-6909.
Wu, Y.; Zhou, J.; Fishkin, N.; Rittman, B. E.; Sparrow, J. R. J. Am. Chem. Soc. 2011, 133, 849-857.
Sparrow, J. R.; Zhou, J.; Ben-Shabat, S.; Vollmer, H., Itagaki, Y.; Nakanishi, K. Invest. Ophthalmol. Visual Sci. 2002, 43, 1222-1227.
Rozanowska, M.; Jarvis-Evans, J.; Korytowski, W.; Boulton, M. E.; Burke, J. M.; Sarna, T. J. Biol. Chem. 1995, 270, 18825-18830.
Moiseyev, G.; Nikolaeva, O.; Chen, Y.; Farjo, K.; Takahashi, Ma, J-X. Proc. Natl. Acad. Sci. U.S.A. 2010, 107, 17551-17556.
Iriyama, A.; Fujiki, R.; Takahashi, H.; Tamaki, Y.; Takezawa, S.; Takeyama, K.; Jang, W-D.; Kato, S.; Yanagi, Y. J. Biol. Chem. 2008, 283, 11947-11953.
Liu, Z.; Ueda, K.; Kim, H. J.; Sparrow, J. R. PLoS One 2015, 10, e138081.
Huta, B. P.; Roberts, A M.; Waters, E. S.; Yu, V. Y.; R. P. Doyle.; Mehlenbacher, M. R.; Bou-Abdallah. F. Med Chem Comm 2014, 5, 787-791.
Huta, B. P.; Mehlenbacher, M. R.; Nie, Y.; Lai, X.; Zubieta, C.; R. P. Doyle.; Bou-Abdallah. F. Chem Med Chem 2016, 11, 277-282.
Kishimoto, Y.; Hiraiwa, M.; O'Brien, J. S. J. Lipid. Res. 1992, 33, 1255-1267.
Weiter, J. J.; Feingold, M.; Kolodny, E. H.; Raghaven, S. S. Am. J. Ophthalmol. 1980, 90, 768-772.
Winzeler, A. M.; Mandemakers, W. J.; Sun, M. Z.; Stafford, M.; Phillips, C. T.; Barres, B. A. The J. Neuroscience 2011, 31, 6481-6492.
Jin, G.; Kubo, H.; Kashiba, M.; Horinouchi, R.; Hasegawa, M.; Suzuki, M.; Sagawa, T.; Oizumi, M.; Fujisawa, A.; Tsukamoto, H.; Yoshimura, S, Yamamoto, Y. J. Clin. Biochem. Nutr. 2008, 42, 167-174.
Parish, C. A.; Hashimoto, M.; Nakanishi, K.; Dillon, J.; Sparrow, J. R. Proc. Natl. Acad. Sci. U.S.A. 1998, 95, 14609-14613.
Dixson, D. D.; Yu, V. Y.; Doyle, R. P. Anal. Biochem. 2011, 419, 145-152.
Veitch, N. C. Phytochem. 2004, 65, 249-259.
Carlsen, C. U.; Moller, J. K. S.; Skibsted, L. H. Coord. Chem. Rev. 2005, 249, 485-498.
Kashiba, M.; Oizumi, M.; Suzuki, M.; Sawamura, Y.; Nagashima, K.; Yoshimura, S.; Yamamoto, Y. J. Clin. Biochem. Nutr. 2014, 55, 85-89.
Bermann, M.; Schutt, F.; Holz, F. G.; Kopitz, J. Exp. Eye. Res. 2001, 72, 191-195.
Holz, F. G.; Schutt, F.; Kopitz, J.; Eldred, G. E.; Kruse, F. E.; Volcker, H. E.; Cantz, M. Invest. Ophthalmol. Vis. Sci. 1999, 40, 737-743.
Louis, A. I.; Fluharty, A. L. Dev. Neurosci. 1991, 13, 41-46.

We claim:

1. A method of treating a disease associated with accumulation of a bisretinoid, comprising:
administering an interfering compound selected from the group consisting of hydroxychloroquine (HCQ), chloroquine (CQ), atovaquone (ATO), apo-carotenal (ACar), Coenzyme Q4 (CoQ4), Coenzyme Q9 (CoQ9), Coenzyme (CoQ10), phosphatidylethanolamine (PEth), phosphatidyl-choline (PCho), and pharmaceutically acceptable salts thereof to a patient; and administering a degrading compound or a pharmaceutically acceptable salt thereof to the patient.

2. The method of claim 1, wherein the interfering compound further includes a pharmaceutically acceptable carrier.

3. The method of claim 1, wherein the disease affects a mammal's eye.

4. The method of claim 3, wherein the disease is selected from the group consisting of macular degeneration, Stargardt disease (SD), and Best vitelliform macular dystrophy.

5. The method of claim 4, wherein the bisretinoid is A2E.

6. The method of claim 1, wherein the degrading compound is an enzyme.

7. The method of claim 6, wherein the degrading compound is horse radish peroxidase.

8. The method of claim 7, wherein the degrading compound is administered intraocularly.

9. The method of claim 8, wherein the interfering compound is administered intraocularly.

10. The method of claim 9, wherein the degrading compound is administered before the interfering compound.

11. The method of claim 9, wherein the degrading compound is co-administered with the interfering compound.

* * * * *